US009687652B2

(12) United States Patent
Franke et al.

(10) Patent No.: US 9,687,652 B2
(45) Date of Patent: Jun. 27, 2017

(54) STIMULATION PATTERNS FOR TREATING DRY EYE

(71) Applicant: Oculeve, Inc., South San Francisco, CA (US)

(72) Inventors: Manfred Franke, Glendale, CA (US); James Donald Loudin, Colma, CA (US); Jarren Armond Baldwin, Oakland, CA (US)

(73) Assignee: Oculeve, Inc., South San Francisco, CA (US)

( * ) Notice: Subject to any disclaimer, the term of this patent is extended or adjusted under 35 U.S.C. 154(b) by 0 days.

(21) Appl. No.: 14/809,109

(22) Filed: Jul. 24, 2015

(65) Prior Publication Data

US 2016/0022992 A1 Jan. 28, 2016

Related U.S. Application Data

(60) Provisional application No. 62/029,362, filed on Jul. 25, 2014, provisional application No. 62/067,416, filed on Oct. 22, 2014.

(51) Int. Cl.
*A61N 1/36* (2006.01)
*A61N 1/05* (2006.01)
*A61N 1/375* (2006.01)

(52) U.S. Cl.
CPC ........ *A61N 1/36046* (2013.01); *A61N 1/0526* (2013.01); *A61N 1/0546* (2013.01); *A61N 1/3606* (2013.01); *A61N 1/36146* (2013.01); *A61N 1/3756* (2013.01)

(58) Field of Classification Search
CPC ... A61N 1/05; A61N 1/18; A61N 1/36; A61N 1/372; A61N 1/0543; A61N 1/36017; A61N 1/36046; A61N 1/3605; A61N 1/36071; A61N 1/0526; A61N 1/3606; A61N 1/36146
USPC ............................ 607/46, 53, 116, 135, 141
See application file for complete search history.

(56) References Cited

U.S. PATENT DOCUMENTS

| 3,620,219 | A | 11/1971 | Barker |
| 3,709,228 | A | 1/1973 | Barker |
| 3,885,550 | A | 5/1975 | MacLeod |
| D257,495 | S | 11/1980 | Bros et al. |
| 4,495,676 | A | 1/1985 | Hartmetz |
| 4,520,825 | A | 6/1985 | Thompson et al. |

(Continued)

FOREIGN PATENT DOCUMENTS

| EM | 2102681-0001 | 10/2012 |
| EM | 2199000-0001 | 3/2013 |

(Continued)

OTHER PUBLICATIONS

Amparo (2013). "Topical Interleukin 1 Receptor Antagonist for Treatment of Dry Eye Disease," JAMA Ophth. 131(6):E1-E9.

(Continued)

*Primary Examiner* — Edward Moran
*Assistant Examiner* — Roland Dinga

(57) ABSTRACT

Described herein are electrical stimulation patterns and methods of use thereof for treating dry eye disease, tired eye, or other forms of ocular discomfort. The methods generally include applying patterned stimulation to an anatomical structure located in an ocular region or a nasal region to increase tear production.

3 Claims, 22 Drawing Sheets

(56) References Cited

U.S. PATENT DOCUMENTS

| | | |
|---|---|---|
| 4,539,988 A | 9/1985 | Shirley et al. |
| 4,590,942 A | 5/1986 | Brenman et al. |
| 4,628,933 A | 12/1986 | Michelson |
| 4,681,121 A | 7/1987 | Kobal |
| 4,684,362 A | 8/1987 | Holt |
| 4,706,680 A | 11/1987 | Keusch et al. |
| 4,735,207 A | 4/1988 | Nambu et al. |
| 4,777,954 A | 10/1988 | Keusch et al. |
| 4,780,932 A | 11/1988 | Bowman et al. |
| 4,868,154 A | 9/1989 | Gilbard et al. |
| 4,926,880 A | 5/1990 | Claude et al. |
| 4,988,358 A | 1/1991 | Eppley et al. |
| 5,025,807 A | 6/1991 | Zabara |
| 5,072,724 A | 12/1991 | Marcus |
| 5,078,733 A | 1/1992 | Eveleigh et al. |
| 5,090,422 A | 2/1992 | Dahl et al. |
| 5,099,829 A | 3/1992 | Wu |
| 5,147,284 A | 9/1992 | Fedorov et al. |
| 5,324,316 A | 6/1994 | Schulman et al. |
| 5,342,410 A | 8/1994 | Braverman |
| 5,345,948 A | 9/1994 | O'Donnell, Jr. |
| 5,360,438 A | 11/1994 | Fisher |
| 5,498,681 A | 3/1996 | Askari et al. |
| 5,514,131 A | 5/1996 | Edwards et al. |
| 5,533,470 A | 7/1996 | Rose |
| 5,545,617 A | 8/1996 | Dartt et al. |
| 5,571,101 A | 11/1996 | Ellman et al. |
| 5,607,461 A | 3/1997 | Lathrop |
| 5,640,978 A | 6/1997 | Wong |
| 5,683,436 A | 11/1997 | Mendes et al. |
| 5,707,400 A | 1/1998 | Terry et al. |
| 5,713,833 A | 2/1998 | Milligan |
| 5,720,773 A | 2/1998 | Lopez-Claros |
| 5,733,282 A | 3/1998 | Ellman et al. |
| 5,735,817 A | 4/1998 | Shantha |
| 5,792,100 A | 8/1998 | Shantha |
| 5,794,614 A | 8/1998 | Gruenke et al. |
| 5,800,685 A | 9/1998 | Perrault |
| 5,843,140 A | 12/1998 | Strojnik |
| 5,900,407 A | 5/1999 | Yerxa et al. |
| 5,904,658 A | 5/1999 | Niederauer et al. |
| 5,948,006 A | 9/1999 | Mann |
| 6,001,088 A | 12/1999 | Roberts et al. |
| 6,020,445 A | 2/2000 | Vanderlaan et al. |
| 6,035,236 A | 3/2000 | Jarding et al. |
| 6,050,999 A | 4/2000 | Paraschac et al. |
| 6,051,017 A | 4/2000 | Loeb et al. |
| 6,083,251 A | 7/2000 | Shindo |
| 6,102,847 A | 8/2000 | Stielau |
| 6,152,916 A | 11/2000 | Bige |
| 6,205,359 B1 | 3/2001 | Boveja |
| 6,208,902 B1 | 3/2001 | Boveja |
| 6,240,316 B1 | 5/2001 | Richmond et al. |
| 6,246,911 B1 | 6/2001 | Seligman |
| 6,270,796 B1 | 8/2001 | Weinstein |
| 6,272,382 B1 | 8/2001 | Faltys et al. |
| 6,275,737 B1 | 8/2001 | Mann |
| 6,277,855 B1 | 8/2001 | Yerxa |
| 6,284,765 B1 | 9/2001 | Caffrey |
| 6,324,429 B1 | 11/2001 | Shire et al. |
| 6,327,504 B1 | 12/2001 | Dolgin et al. |
| 6,366,814 B1 | 4/2002 | Boveja et al. |
| 6,405,079 B1 | 6/2002 | Ansarinia et al. |
| 6,458,157 B1 | 10/2002 | Suaning |
| 6,505,077 B1 | 1/2003 | Kast et al. |
| 6,526,318 B1 | 2/2003 | Ansarinia et al. |
| 6,535,766 B1 | 3/2003 | Thompson et al. |
| 6,537,265 B2 | 3/2003 | Thanavala et al. |
| 6,539,253 B2 | 3/2003 | Thompson et al. |
| 6,562,036 B1 | 5/2003 | Ellman et al. |
| 6,564,102 B1 | 5/2003 | Boveja |
| 6,578,579 B2 | 6/2003 | Burnside et al. |
| 6,604,528 B1 | 8/2003 | Duncan |
| 6,641,799 B2 | 11/2003 | Goldberg |
| 6,658,301 B2 | 12/2003 | Loeb et al. |
| 6,662,052 B1 | 12/2003 | Sarwal et al. |
| 6,684,879 B1 | 2/2004 | Coffee et al. |
| 6,701,189 B2 | 3/2004 | Fang et al. |
| 6,748,951 B1 | 6/2004 | Schmidt |
| 6,792,314 B2 | 9/2004 | Byers et al. |
| 6,829,508 B2 | 12/2004 | Schulman et al. |
| 6,853,858 B2 | 2/2005 | Shalev |
| 6,871,099 B1 | 3/2005 | Whitehurst et al. |
| 6,879,859 B1 | 4/2005 | Boveja |
| 6,885,888 B2 | 4/2005 | Rezai |
| 6,895,279 B2 | 5/2005 | Loeb et al. |
| 7,024,241 B1 | 4/2006 | Bornzin et al. |
| 7,054,692 B1 | 5/2006 | Whitehurst et al. |
| 7,067,307 B2 | 6/2006 | Hochleitner et al. |
| 7,069,084 B2 | 6/2006 | Yee |
| 7,117,033 B2 | 10/2006 | Shalev et al. |
| 7,142,909 B2 | 11/2006 | Greenberg et al. |
| 7,146,209 B2 | 12/2006 | Gross et al. |
| 7,169,163 B2 | 1/2007 | Becker |
| 7,190,998 B2 | 3/2007 | Shalev et al. |
| 7,225,032 B2 | 5/2007 | Schmeling et al. |
| 7,228,184 B2 | 6/2007 | Heath |
| 7,247,692 B2 | 7/2007 | Laredo |
| 7,317,947 B2 | 1/2008 | Wahlstrand et al. |
| 7,330,762 B2 | 2/2008 | Boveja et al. |
| 7,346,398 B2 | 3/2008 | Gross et al. |
| 7,369,897 B2 | 5/2008 | Boveja et al. |
| 7,442,191 B2 | 10/2008 | Hovda et al. |
| 7,460,911 B2 | 12/2008 | Cosendai et al. |
| 7,477,947 B2 | 1/2009 | Pines et al. |
| 7,502,652 B2 | 3/2009 | Gaunt et al. |
| 7,547,447 B2 | 6/2009 | Yiu et al. |
| 7,565,204 B2 | 7/2009 | Matei et al. |
| 7,599,737 B2 | 10/2009 | Yomtov et al. |
| 7,636,597 B2 | 12/2009 | Gross et al. |
| 7,650,186 B2 | 1/2010 | Hastings et al. |
| D613,408 S | 4/2010 | Gausmann et al. |
| D614,303 S | 4/2010 | Gausmann et al. |
| D614,774 S | 4/2010 | Gausmann et al. |
| 7,725,176 B2 | 5/2010 | Schuler et al. |
| 7,725,195 B2 | 5/2010 | Lima et al. |
| D617,443 S | 6/2010 | Grenon et al. |
| 7,758,190 B2 | 7/2010 | Korb et al. |
| 7,778,703 B2 | 8/2010 | Gross et al. |
| 7,778,711 B2 | 8/2010 | Ben-David et al. |
| 7,792,591 B2 | 9/2010 | Rooney et al. |
| 7,805,200 B2 | 9/2010 | Kast et al. |
| 7,805,202 B2 | 9/2010 | Kuzma et al. |
| 7,805,203 B2 | 9/2010 | Ben-David et al. |
| 7,809,442 B2 | 10/2010 | Bolea et al. |
| 7,835,794 B2 | 11/2010 | Greenberg et al. |
| 7,846,124 B2 | 12/2010 | Becker |
| 7,860,570 B2 | 12/2010 | Whitehurst et al. |
| 7,873,421 B2 | 1/2011 | Karell |
| 7,879,079 B2 | 2/2011 | Tu et al. |
| D638,128 S | 5/2011 | Prokop et al. |
| 7,981,095 B2 | 7/2011 | Grenon et al. |
| 7,993,381 B2 | 8/2011 | Mac et al. |
| 7,998,202 B2 | 8/2011 | Lesh |
| 8,002,783 B2 | 8/2011 | Vercellotti et al. |
| 8,019,419 B1 | 9/2011 | Panescu et al. |
| 8,019,441 B2 | 9/2011 | Wallace et al. |
| 8,080,047 B2 | 12/2011 | Yu |
| 8,145,322 B1 | 3/2012 | Yao et al. |
| 8,155,746 B2 | 4/2012 | Maltan et al. |
| 8,165,680 B2 | 4/2012 | Greenberg et al. |
| 8,204,591 B2 | 6/2012 | Ben-David et al. |
| 8,231,218 B2 | 7/2012 | Hong et al. |
| 8,251,983 B2 | 8/2012 | Larson et al. |
| 8,295,529 B2 | 10/2012 | Petersen et al. |
| 8,318,070 B2 | 11/2012 | Shiah et al. |
| D681,839 S | 5/2013 | Nathanson |
| 8,489,189 B2 | 7/2013 | Tronnes |
| 8,494,641 B2 | 7/2013 | Boling et al. |
| 8,626,298 B2 | 1/2014 | Simon |
| 8,676,324 B2 | 3/2014 | Simon et al. |
| 8,728,136 B2 | 5/2014 | Feldman |
| 8,918,181 B2 | 12/2014 | Ackermann et al. |
| 8,936,594 B2 | 1/2015 | Wolf et al. |

(56) References Cited

U.S. PATENT DOCUMENTS

| | | |
|---|---|---|
| 8,986,301 B2 | 3/2015 | Wolf et al. |
| 8,996,137 B2 | 3/2015 | Ackermann et al. |
| 9,079,042 B2 | 7/2015 | Tiedtke et al. |
| 9,095,723 B2 | 8/2015 | Ackermann et al. |
| 9,265,956 B2 | 2/2016 | Ackermann et al. |
| 9,440,065 B2 | 9/2016 | Ackermann et al. |
| 2001/0020177 A1 | 9/2001 | Gruzdowich et al. |
| 2002/0013594 A1 | 1/2002 | Dinger et al. |
| 2002/0035358 A1 | 3/2002 | Wang |
| 2002/0049290 A1 | 4/2002 | Vanderbilt et al. |
| 2002/0188331 A1 | 12/2002 | Fang et al. |
| 2003/0045909 A1 | 3/2003 | Gross et al. |
| 2003/0114899 A1 | 6/2003 | Woods et al. |
| 2003/0120323 A1 | 6/2003 | Meadows et al. |
| 2003/0130809 A1 | 7/2003 | Cohen et al. |
| 2003/0192784 A1 | 10/2003 | Zhou et al. |
| 2003/0233134 A1 | 12/2003 | Greenberg et al. |
| 2004/0059466 A1 | 3/2004 | Block et al. |
| 2004/0098036 A1 | 5/2004 | Bergersen |
| 2004/0098067 A1 | 5/2004 | Ohta et al. |
| 2004/0138646 A1 | 7/2004 | Walla |
| 2004/0147973 A1 | 7/2004 | Hauser et al. |
| 2004/0151930 A1 | 8/2004 | Rouns et al. |
| 2004/0220644 A1 | 11/2004 | Shalev et al. |
| 2005/0004621 A1 | 1/2005 | Boveja et al. |
| 2005/0010250 A1 | 1/2005 | Schuler et al. |
| 2005/0010266 A1 | 1/2005 | Bogdanowicz |
| 2005/0101967 A1 | 5/2005 | Weber et al. |
| 2005/0101994 A1 | 5/2005 | Yamazaki et al. |
| 2005/0105046 A1 | 5/2005 | Tung |
| 2005/0137276 A1 | 6/2005 | Yahiaoui et al. |
| 2005/0159790 A1 | 7/2005 | Shalev et al. |
| 2005/0197675 A1 | 9/2005 | David et al. |
| 2005/0251061 A1 | 11/2005 | Schuler et al. |
| 2005/0267542 A1 | 12/2005 | David et al. |
| 2005/0268472 A1 | 12/2005 | Bourilkov et al. |
| 2006/0004423 A1 | 1/2006 | Boveja et al. |
| 2006/0018872 A1 | 1/2006 | Tew et al. |
| 2006/0074450 A1 | 4/2006 | Boveja et al. |
| 2006/0089673 A1 | 4/2006 | Schultheiss et al. |
| 2006/0095077 A1 | 5/2006 | Tronnes et al. |
| 2006/0095108 A1 | 5/2006 | Chowdhury et al. |
| 2006/0100668 A1 | 5/2006 | Ben-David et al. |
| 2006/0107958 A1 | 5/2006 | Sleeper |
| 2006/0142822 A1 | 6/2006 | Tulgar |
| 2006/0161225 A1 | 7/2006 | Sormann et al. |
| 2006/0195169 A1 | 8/2006 | Gross et al. |
| 2006/0206155 A1 | 9/2006 | Ben-David et al. |
| 2006/0216317 A1 | 9/2006 | Reinhard et al. |
| 2006/0235430 A1 | 10/2006 | Le et al. |
| 2006/0239482 A1* | 10/2006 | Hatoum ............. A61N 1/37229 381/312 |
| 2006/0259098 A1 | 11/2006 | Erickson |
| 2006/0271024 A1 | 11/2006 | Gertner et al. |
| 2006/0271108 A1 | 11/2006 | Libbus et al. |
| 2007/0038267 A1 | 2/2007 | Shodo et al. |
| 2007/0060815 A1 | 3/2007 | Martin et al. |
| 2007/0060954 A1 | 3/2007 | Cameron et al. |
| 2007/0083245 A1 | 4/2007 | Lamensdorf et al. |
| 2007/0150034 A1 | 6/2007 | Rooney et al. |
| 2007/0219600 A1 | 9/2007 | Gertner et al. |
| 2007/0237797 A1 | 10/2007 | Peyman |
| 2007/0237825 A1 | 10/2007 | Levy et al. |
| 2007/0248930 A1 | 10/2007 | Brawn |
| 2007/0250119 A1* | 10/2007 | Tyler ................. A61N 1/36014 607/2 |
| 2007/0250135 A1 | 10/2007 | Bartz-Schmidt et al. |
| 2007/0276314 A1 | 11/2007 | Becker |
| 2007/0276451 A1 | 11/2007 | Rigaux |
| 2007/0295327 A1 | 12/2007 | Bottomley |
| 2007/0299462 A1 | 12/2007 | Becker |
| 2008/0009897 A1 | 1/2008 | Duran Von Arx |
| 2008/0021515 A1 | 1/2008 | Horsager et al. |
| 2008/0082131 A1 | 4/2008 | Llanos |
| 2008/0109054 A1 | 5/2008 | Hastings et al. |
| 2008/0132933 A1 | 6/2008 | Gerber |
| 2008/0140141 A1 | 6/2008 | Ben-David et al. |
| 2008/0183242 A1 | 7/2008 | Tano et al. |
| 2008/0183243 A1 | 7/2008 | Shodo et al. |
| 2008/0269648 A1 | 10/2008 | Bock |
| 2009/0005835 A1 | 1/2009 | Greenberg et al. |
| 2009/0012573 A1 | 1/2009 | Karell et al. |
| 2009/0018582 A1 | 1/2009 | Ishikawa et al. |
| 2009/0024187 A1 | 1/2009 | Erickson et al. |
| 2009/0024189 A1* | 1/2009 | Lee .................. A61N 1/36017 607/66 |
| 2009/0043185 A1 | 2/2009 | McAdams et al. |
| 2009/0056709 A1 | 3/2009 | Worsoff |
| 2009/0099600 A1 | 4/2009 | Moore et al. |
| 2009/0099623 A1 | 4/2009 | Bentwich et al. |
| 2009/0099626 A1 | 4/2009 | de Juan, Jr. et al. |
| 2009/0101139 A1 | 4/2009 | Karell |
| 2009/0124965 A1 | 5/2009 | Greenberg et al. |
| 2009/0138061 A1 | 5/2009 | Stephens et al. |
| 2009/0156581 A1 | 6/2009 | Dillon et al. |
| 2009/0157142 A1 | 6/2009 | Cauller et al. |
| 2009/0157145 A1 | 6/2009 | Cauller |
| 2009/0157147 A1 | 6/2009 | Cauller et al. |
| 2009/0192571 A1 | 7/2009 | Stett et al. |
| 2009/0204142 A1 | 8/2009 | Becker |
| 2009/0241840 A1 | 10/2009 | Mills |
| 2009/0264966 A1 | 10/2009 | Blum et al. |
| 2009/0281594 A1 | 11/2009 | King et al. |
| 2009/0281596 A1 | 11/2009 | King et al. |
| 2009/0299418 A1 | 12/2009 | Shalev et al. |
| 2009/0306738 A1 | 12/2009 | Weiss et al. |
| 2010/0030150 A1 | 2/2010 | Paques et al. |
| 2010/0076423 A1 | 3/2010 | Muller |
| 2010/0087896 A1 | 4/2010 | McCreery |
| 2010/0094280 A1 | 4/2010 | Muller |
| 2010/0139002 A1 | 6/2010 | Walker et al. |
| 2010/0152708 A1 | 6/2010 | Li et al. |
| 2010/0161004 A1 | 6/2010 | Najafi et al. |
| 2010/0168513 A1 | 7/2010 | Pless et al. |
| 2010/0179468 A1 | 7/2010 | Becker |
| 2010/0274164 A1 | 10/2010 | Juto |
| 2010/0274313 A1 | 10/2010 | Boling et al. |
| 2010/0280509 A1 | 11/2010 | Muller et al. |
| 2010/0288275 A1 | 11/2010 | Djupesland et al. |
| 2010/0318159 A1 | 12/2010 | Aghassian et al. |
| 2011/0021975 A1 | 1/2011 | Covello |
| 2011/0028807 A1 | 2/2011 | Abreu |
| 2011/0028883 A1 | 2/2011 | Juan, Jr. et al. |
| 2011/0077551 A1 | 3/2011 | Videbaek |
| 2011/0093043 A1 | 4/2011 | Torgerson et al. |
| 2011/0151393 A1 | 6/2011 | Frey, II et al. |
| 2011/0152969 A1 | 6/2011 | Zehnder et al. |
| 2011/0202121 A1 | 8/2011 | Wen |
| 2011/0218590 A1 | 9/2011 | Degiorgio et al. |
| 2011/0234971 A1 | 9/2011 | Yeh |
| 2011/0275734 A1 | 11/2011 | Scales et al. |
| 2011/0276107 A1 | 11/2011 | Simon et al. |
| 2011/0282251 A1 | 11/2011 | Baker et al. |
| 2011/0295336 A1 | 12/2011 | Sharma et al. |
| 2011/0313330 A1 | 12/2011 | Loushin et al. |
| 2011/0313481 A1 | 12/2011 | De Vos |
| 2012/0053648 A1 | 3/2012 | Neher et al. |
| 2012/0130398 A1 | 5/2012 | Ackermann et al. |
| 2012/0197338 A1 | 8/2012 | Su et al. |
| 2012/0232615 A1 | 9/2012 | Barolat et al. |
| 2012/0232618 A1 | 9/2012 | Feldman |
| 2012/0234332 A1 | 9/2012 | Shantha |
| 2012/0253249 A1 | 10/2012 | Wilson |
| 2012/0298105 A1 | 11/2012 | Osorio |
| 2012/0315329 A1 | 12/2012 | Ahn et al. |
| 2012/0316557 A1 | 12/2012 | Sartor et al. |
| 2012/0323214 A1 | 12/2012 | Shantha |
| 2012/0323227 A1 | 12/2012 | Wolf et al. |
| 2012/0323232 A1 | 12/2012 | Wolf et al. |
| 2012/0330376 A1 | 12/2012 | Flynn et al. |
| 2013/0006095 A1 | 1/2013 | Jenkins et al. |
| 2013/0006326 A1 | 1/2013 | Ackermann et al. |
| 2013/0053737 A1 | 2/2013 | Scerbo |
| 2013/0065765 A1 | 3/2013 | Selifonov et al. |

(56) References Cited

U.S. PATENT DOCUMENTS

| | | |
|---|---|---|
| 2013/0158451 A1 | 6/2013 | Juto et al. |
| 2013/0158626 A1 | 6/2013 | DeGiorgio et al. |
| 2013/0172790 A1 | 7/2013 | Badawi |
| 2013/0178937 A1 | 7/2013 | Vassallo et al. |
| 2013/0253387 A1 | 9/2013 | Bonutti et al. |
| 2013/0261706 A1 | 10/2013 | Mirro et al. |
| 2013/0270491 A1 | 10/2013 | Park et al. |
| 2013/0304154 A1 | 11/2013 | Goodman et al. |
| 2013/0310887 A1 | 11/2013 | Curtis |
| 2014/0012182 A1 | 1/2014 | Shantha et al. |
| 2014/0081353 A1 | 3/2014 | Cook et al. |
| 2014/0088463 A1 | 3/2014 | Wolf et al. |
| 2014/0163580 A1 | 6/2014 | Tischendorf et al. |
| 2014/0214120 A1 | 7/2014 | Simon et al. |
| 2014/0257433 A1 | 9/2014 | Ackermann et al. |
| 2014/0277429 A1 | 9/2014 | Kuzma et al. |
| 2014/0316310 A1 | 10/2014 | Ackermann et al. |
| 2014/0316396 A1 | 10/2014 | Wolf et al. |
| 2014/0316485 A1 | 10/2014 | Ackermann et al. |
| 2014/0371812 A1 | 12/2014 | Ackermann et al. |
| 2015/0088156 A1 | 3/2015 | Ackermann et al. |
| 2015/0238754 A1 | 8/2015 | Loudin et al. |
| 2015/0335900 A1 | 11/2015 | Ackermann et al. |
| 2016/0022992 A1 | 1/2016 | Franke et al. |
| 2016/0114163 A1 | 4/2016 | Franke et al. |
| 2016/0114172 A1 | 4/2016 | Loudin et al. |
| 2016/0121118 A1 | 5/2016 | Franke et al. |
| 2016/0158548 A1 | 6/2016 | Ackermann et al. |
| 2016/0367795 A1 | 12/2016 | Ackermann et al. |

FOREIGN PATENT DOCUMENTS

| | | |
|---|---|---|
| EP | 0109935 A1 | 5/1984 |
| EP | 1497483 | 1/2005 |
| EP | 1651307 | 5/2006 |
| EP | 1919553 | 5/2008 |
| EP | 1958661 A1 | 8/2008 |
| EP | 2205193 | 7/2010 |
| EP | 2205314 | 7/2010 |
| GB | 2 129 690 B | 3/1987 |
| JP | 2002-325851 A | 11/2002 |
| JP | 2002-539859 A | 11/2002 |
| JP | 2005-052461 A | 3/2005 |
| JP | 2006-515900 A | 6/2006 |
| JP | 2007-044323 A | 2/2007 |
| JP | 2007-528751 A | 10/2007 |
| JP | 2008-183248 A | 8/2008 |
| JP | 2008-541850 A | 11/2008 |
| JP | 2010-505563 A | 2/2010 |
| JP | 2010-051562 A | 3/2010 |
| JP | 2010-537777 A | 12/2010 |
| JP | 2011-030734 A | 2/2011 |
| WO | WO-00/56393 A1 | 9/2000 |
| WO | WO-00/62672 A1 | 10/2000 |
| WO | WO-03/087433 A1 | 10/2003 |
| WO | WO-2004/026106 A2 | 4/2004 |
| WO | WO-2004/026106 A3 | 4/2004 |
| WO | WO-2004/043217 A2 | 5/2004 |
| WO | WO-2004/043217 A3 | 5/2004 |
| WO | WO-2004/091453 A1 | 10/2004 |
| WO | WO-2004/112893 A2 | 12/2004 |
| WO | WO-2004/112893 A3 | 12/2004 |
| WO | WO-2005/007234 A2 | 1/2005 |
| WO | WO-2005/007234 A3 | 1/2005 |
| WO | WO-2005/030025 A2 | 4/2005 |
| WO | WO-2005/030025 A3 | 4/2005 |
| WO | WO-2005/060984 A1 | 7/2005 |
| WO | WO-2006/127366 A1 | 11/2006 |
| WO | WO-2008/156501 A2 | 12/2008 |
| WO | WO-2008/156501 A3 | 12/2008 |
| WO | WO-2009/035571 A2 | 3/2009 |
| WO | WO-2009/035571 A3 | 3/2009 |
| WO | WO-2009/070709 A1 | 6/2009 |
| WO | WO-2010/003011 A1 | 1/2010 |
| WO | WO-2010/027743 A1 | 3/2010 |
| WO | WO-2010/099818 A1 | 9/2010 |
| WO | WO-2011/011373 A1 | 1/2011 |
| WO | WO-2012/068247 A1 | 5/2012 |
| WO | WO-2012/139063 A2 | 10/2012 |
| WO | WO-2012/139063 A3 | 10/2012 |
| WO | WO-2013/055940 A2 | 4/2013 |
| WO | WO-2013/055940 A3 | 4/2013 |
| WO | WO-2013/165697 A1 | 11/2013 |
| WO | WO-2014/138709 A1 | 9/2014 |
| WO | WO-2014/165124 A1 | 10/2014 |
| WO | WO-2014/172693 A2 | 10/2014 |
| WO | WO-2014/172693 A3 | 10/2014 |
| WO | WO-2015/130707 A2 | 9/2015 |
| WO | WO-2015/130707 A3 | 9/2015 |
| WO | WO-2016/015025 A1 | 1/2016 |
| WO | WO-2016/065211 A1 | 4/2016 |
| WO | WO-2016/065213 A1 | 4/2016 |
| WO | WO-2016/065215 A1 | 4/2016 |

OTHER PUBLICATIONS

Australian Office Action received for Australian Patent Application No. 2011328900, mailed on Feb. 28, 2014.

Australian Office Action Received for Australian Patent Application No. 2012239966, mailed on Mar. 17, 2014.

Australian Office Action received for Australian Patent Application No. 2015203140, issued on Mar. 17, 2016.

Australian Office Action received for Australian Patent Application No. 2015203275, mailed on Mar. 23, 2016.

Bajpai et al. (2012). "Preparation, Characterization and Water Uptake Behavior of Polysaccharide Based Nanoparticles," Prog. Nanotech. Nanomat. 1(1):9-17.

Baraniuk et al. (2007). "Nasonasal Reflexes, the Nasal Cycle, and Sneeze," Curr. Allergy and Asthma Reports 7:105-111.

Calonge (2001). "The Treatment of Dry Eye," Survey Ophth. 45(2)S227-S239.

Chinese Office Action Received for Chinese Patent Application No. 201180064627.8, mailed on Feb. 2, 2015.

Chinese Office Action Received for Chinese Patent Application No. 201180064627.8, mailed on Jun. 20, 2014.

Chinese Office Action Received for Chinese Patent Application No. 201180064627.8, mailed on Jun. 30, 2015.

Chinese Office Action received for Chinese Patent Application No. 201280028006.9, mailed on Jul. 1, 2015.

Chinese Office Action received for Chinese Patent Application No. 201280028006.9, mailed on Nov. 14, 2014.

Cipriano et al. (2014). "Superabsorbent Hydrogels That Are Robust and Highly Stretchable," Am. Chem Soc. 47(13):4445-4452.

Dart et al. (2002). "Effects of 25% Propylene Glycol Hydrogel (Solugel) on Second Intention Wound Healing in Horses," Vet. Surg. 31(4):309-313.

Elsby et al. (1967). "Lacrimal Secretion in the Cat," Br. J. Pharm. Chemother. 29(1):1-7.

Extended European Search Report (includes Supplementary European Search Report and Search Opinion) received for European Patent Application No. 11842076.9, mailed on Oct. 10, 2014.

Final Office Action received for U.S. Appl. No. 13/441,806, mailed on Mar. 12, 2015.

Final Office Action received for U.S. Appl. No. 13/441,806, mailed on May 20, 2016.

Final Office Action received for U.S. Appl. No. 14/256,916, mailed on Apr. 8, 2015.

Final Office Action received for U.S. Appl. No. 14/313,937 mailed on Apr. 29, 2015.

Final Office Action received for U.S. Appl. No. 14/816,846, mailed on May 11, 2016.

Fujisawa et al. (2002). "The Effect of Nasal Mucosal Stimulation on Schirmer Tests in Sjogren's Syndrome and Dry Eye Patients," Lac. Gland Tear Film Dry Eye Syndrome 3 506:1221-1226.

Gupta et al. (1997). "Nasolacrimal Stimulation of Aqueous Tear Production," Cornea 16(6):645-648.

Ikemura et al. (2008). "UV-VIS Spectra and Photoinitiation Behaviors of Acylphosphine Oxide and Bisacylphosphine Oxide Derivatives in unfilled, Light-Cured Dental Resins," Dental Mat. J. 27(6):765-774.

(56) References Cited

OTHER PUBLICATIONS

International Preliminary Report on Patentability received for PCT Application No. PCT/US2014/022158, mailed on Sep. 17, 2015.
International Preliminary Report on Patentability received for PCT Patent Application No. PCT/US2011/060989, mailed on May 30, 2013.
International Preliminary Report on Patentability received for PCT Patent Application No. PCT/US2012/032629, mailed on Oct. 17, 2013.
International Preliminary Report on Patentability received for PCT Patent Application No. PCT/US2014/034733, mailed on Oct. 29, 2015.
International Search Report & Written Opinion received for PCT Patent Application No. PCT/US2011/060989, mailed on Feb. 23, 2012.
International Search Report & Written Opinion received for PCT Patent Application No. PCT/US2014/022158, mailed on Jul. 30, 2014.
International Search Report and Written Opinion received for PCT Application No. PCT/US2015/042130, mailed on Oct. 28, 2015.
International Search Report and Written Opinion received for PCT Patent Application No. PCT/US2014/034733, mailed on Dec. 5, 2014.
International Search Report and Written Opinion received for PCT Patent Application No. PCT/US2015/017379, mailed on Jul. 24, 2015.
International Search Report and Written Opinion received for PCT Patent Application No. PCT/US2015/057023, mailed on Mar. 4, 2016.
International Search Report received for PCT Patent Application No. PCT/US2012/32629, mailed on Oct. 26, 2012.
International Search Report received for PCT Patent Application No. PCT/US2015/57021, mailed on Feb. 10, 2016.
Extended European Search Report received for European Patent Application No. 12768458.7, mailed on Aug. 28, 2014.
Invitation to Pay Additional Fees received for PCT Application No. PCT/US2012/032629, mailed on Aug. 28, 2012, 2 pages.
Invitation to pay additional fees received for PCT Patent Application No. PCT/US2014/034733, mailed on Sep. 24, 2014.
Invitation to pay additional fees received for PCT Patent Application No. PCT/US2015/017379, mailed on May 22, 2015.
Invitation to Pay Additional Fees received for PCT Patent Application No. PCT/US2015/057023, mailed on Jan. 7, 2016.
Invitation to Pay Additional Fees received for PCT Patent Application No. PCT/US2015/57021, mailed on Dec. 18, 2015.
Japanese Office Action received for Japanese Patent Application No. 2013-539971, mailed on Jun. 20, 2016.
Japanese Office Action received for Japanese Patent Application No. 2013-539971, mailed on Oct. 5, 2015.
Japanese Office Action received for Japanese Patent Application No. 2014-504050, mailed on Mar. 14, 2016.
Lora et al. (2009). "Lacrimal Nerve Stimulation by a Neurostimulator for Tear Production," Invest. Ophth. Vis. Science 50(13):172.
Mallepally et al. (2013). "Superabsorbent Alginate Aerogels," J. Supercritical Fluids 79:1-5.
Non Final Office Action received for U.S. Appl. No. 14/256,915, mailed on Aug. 13, 2014.
Non Final Office Action received for U.S. Appl. No. 14/256,916, mailed on Sep. 12, 2014.
Non Final Office Action received for U.S. Appl. No. 13/441,806, mailed on Sep. 17, 2015.
Non-Final Office Action received for U.S. Appl. No. 13/298,042, mailed on Oct. 2, 2013.
Non-Final Office Action received for U.S. Appl. No. 13/441,806, mailed on Dec. 18, 2013.
Non-Final Office Action received for U.S. Appl. No. 14/201,753, mailed on Apr. 2, 2015.
Non-Final Office Action received for U.S. Appl. No. 14/313,937, mailed on Nov. 19, 2014.
Non-Final Office Action received for U.S. Appl. No. 14/630,471, mailed on Jun. 14, 2016.
Non-Final Office Action received for U.S. Appl. No. 14/809,109, mailed on Apr. 8, 2016.
Non-Final Office Action received for U.S. Appl. No. 14/816,846, mailed on Sep. 11, 2015.
Non-Final Office Action Received for U.S. Appl. No. 14/920,860, mailed Aug. 17, 2016.
Non-Final Office Action received for U.S. Appl. No. 14/256,916, mailed on Nov. 19, 2015.
Non-Final Office Action Received for U.S. Appl. No. 14/313,937, mailed on Oct. 6, 2015.
Non-Final Office Action Received for U.S. Appl. No. 14/920,852, mailed on Aug. 1, 2016.
Notice of Acceptance Received for Australian Patent Application No. 2011328900, mailed on Mar. 10, 2015.
Notice of Acceptance received for Australian Patent Application No. 2012239966, mailed on Nov. 12, 2015.
Notice of Acceptance Received for Australian Patent Application No. 2014253754, mailed on Mar. 10, 2015.
Notice of Allowance received for Chinese Patent Application No. 201180064627.8, mailed on Jun. 30, 2015.
Notice of Allowance received for Chinese Patent Application No. 201280028006.9, mailed on Nov. 16, 2015.
Notice of Allowance received for U.S. Appl. No. 14/313,937, mailed on May 2, 2016.
Notice of Allowance received for U.S. Appl. No. 14/201,753, mailed on Dec. 15, 2015.
Notice of Allowance received for U.S. Appl. No. 14/201,753, mailed on Oct. 15, 2015.
Notice of Allowance received for U.S. Appl. No. 13/298,042, mailed on Apr. 29, 2014.
Notice of Allowance received for U.S. Appl. No. 13/298,042, mailed on Aug. 11, 2014.
Notice of Allowance received for U.S. Appl. No. 13/298,042, mailed on Nov. 13, 2014.
Notice of Allowance received for U.S. Appl. No. 14/256,915, mailed on Nov. 26, 2014.
Notice of Allowance received for U.S. Appl. No. 14/313,937, mailed on Feb. 19, 2016.
Notice of Allowance received for U.S. Appl. No. 14/561,107, mailed on Mar. 31, 2015.
Pasqui et al. (2012). "Polysaccharide-Based Hydrogels: The Key Role of Water in Affecting Mechanical Properties," Polymers 4(3):1517-1534.
Roessler et al. (2009). "Implantation and Explantation of a Wireless Epiretinal Retina Implant Device: Observations During the EPIRET3 Prospective Clinical Trial," Invest. Ophthal. Visual Science 50(6):3003-3008.
Ruskell (2004). "Distribution of Pterygopalatine Ganglion Efferents to the Lacrimal Gland in Man," Exp. Eye Res. 78(3):329-335.
Sall et al. (2000). "Two Multicenter, Randomized Studies of the Efficacy and Safety of Cyclosporine Ophthalmic Emulsion in Moderate to Severe Dry Eye Disease," Ophth. 107(4):631-639.
Shaari et al. (1995). "Rhinorrhea is decreased in dogs after nasal application of botulinum toxin," Oto. Head Neck Surg. 112(4):566-571.
Stjernschantz et al. (1979). "Electrical Stimulation of the Fifth Cranial Nerve in Rabbits: Effects on Ocular Blood Flow, Extravascular Albumin Content and Intraocular Pressure," Exp. Eye Res. 28(2):229-238.
Stjernschantz et al. (1980). "Vasomotor effects of Facial Nerve Stimulation: Noncholinergic Vasodilation in the eye," Acta Phys. Scand. 109(1):45-50.
Tsubota (1991). "The Importance of the Schirmer Test with Nasal Stimulation," Am. J. Ophth. 111:106-108.
Velikay-Parel et al. (2011). "Perceptual Threshold and Neuronal Excitability as Long-Term Safety Evaluation in Retinal Implants." Invest. Opht. Visual Science E-Abstract 2590, 2 pages.
Written Opinion received for PCT Patent Application No. PCT/US2015/57021, mailed on Feb. 10, 2016.
Zilstorff-Pedersen (1965). "Quantitative Measurements of the Nasolacrimal Reflex," Arch. Oto. 81:457-462.

(56) References Cited

OTHER PUBLICATIONS

U.S. Appl. No. 15/256,392, filed Sep. 2, 2016, by Ackermann et al.
Acar, M. et al. (2013). "Ocular surface assessment in patients with obstructive sleep apnea-hypopnea syndrome," Sleep Breath 17(2):583-588.
Baroody, F.M. et al. (2008). "Nasal ocular reflexes and eye symptoms in patients with allergic rhinitis," Ann Allergy Asthma Immunol 100:194-199.
Baroody, F.M. et al. (2009). "Fluticasone furoate nasal spray reduces the nasal-ocular reflex: a mechanism for the efficacy of topical steroids in controlling allergic eye symptoms," J Allergy Clin Immunol 123:1342-1348.
Boberg-Ans, J. (1955). "Experience in clinical examination of corneal sensitivity: corneal sensitivity and the naso-lacrimal reflex after retrobulbar anaesthesia," Br J Ophthalmol 39:705-726.
Drummond, P.D. (1995). "Lacrimation and cutaneous vasodilatation in the face induced by painful stimulation of the nasal ala and upper lip," J Auton Nery Syst 51:109-116.
Extended European Search Report mailed on Nov. 18, 2016, for EP Application No. 14 785 631.4, filed on Apr. 18, 2014, 7 pages.
Extended European Search Report mailed on Oct. 21, 2016, for EP Application No. 14 778 719.6, filed on Mar. 12, 2014, 8 pages.
Final Office Action received for U.S. Appl. No. 14/630,471, mailed on Sep. 26, 2016, 22 pages.
Final Office Action received for U.S. Appl. No. 14/256,916, mailed on Aug. 19, 2016, 19 pages.
Final Office Action mailed on Feb. 1, 2017, for U.S. Appl. No. 14/920,852, filed on Oct. 22, 2015, 20 pages.
Final Office Action received for U.S. Appl. No. 13/441,806, mailed on Mar. 12, 2015, 10 pages.
Final Office Action received for U.S. Appl. No. 13/441,806, mailed on May 20, 2016, 10 pages.
Final Office Action received for U.S. Appl. No. 14/207,072, mailed on Jun. 22, 2016, 20 pages.
Heigle, T.J. et al. (1996). "Aqueous tear production in patients with neurotrophic keratitis," Cornea 15:135-138.
Holzer, P. (1991). "Capsaicin: cellular targets, mechanisms of action, and selectivity for thin sensory neurons," Pharmacol Rev 43:143-201.
International Search Report and Written Opinion received for PCT Patent Application No. PCT/US2014/024496, mailed on Aug. 22, 2014, 11 pages.
International Search Report received for PCT Patent Application No. PCT/US2015/57019, mailed on Feb. 11, 2016, 4 pages.
Krupin, T. et al. (1977). "Decreased basal tear production associated with general anesthesia," Arch Ophthalmol. 95:107-108.
Löth, S. et al. (1994). "Effect of nasal anaesthesia on lacrimal function after nasal allergen challenge," Clin Exp Allergy 24:375-376.
Meng, I.D. et al. (2013). "The role of corneal afferent neurons in regulating tears under normal and dry eye conditions," Exp Eye Res 117:79-87.
Non-Final Office Action mailed on Sep. 30, 2016, for U.S. Appl. No. 15/256,392, filed on Sep. 2, 2016, 14 pages.
Non-Final Office Action mailed on Feb. 14, 2017, for U.S. Appl. No. 14/630,471, filed on Feb. 24, 2015, 23 pages.
Non Final Office Action received for U.S. Appl. No. 13/441,806, mailed on Sep. 17, 2015, 11 pages.
Non-Final Office Action received for U.S. Appl. No. 13/441,806, mailed on Dec. 18, 2013, 9 pages.
Non Final Office Action received for U.S. Appl. No. 14/207,072, mailed on Dec. 9, 2015, 8 pages.
Non-Final Office Action mailed on Sep. 27, 2016, for U.S. Appl. No. 14/920,847, filed on Oct. 22, 2015, 13 pages.
Non-Final Office Action mailed on Nov. 2, 2016, for U.S. Appl. No. 13/441,806, filed on Apr. 6, 2012, 10 pages.
Non-Final Office Action mailed on Dec. 6, 2016, for U.S. Appl. No. 14/816,846, filed on Aug. 3, 2015, 13 pages.
Corrected Notice of Allowability mailed on Feb. 23, 2015, for U.S. Appl. No. 14/256,915, filed on Apr. 18, 2014, 2 pages.
Notice of Allowance mailed on Jan. 19, 2017, for U.S. Appl. No. 14/920,860, filed on Oct. 22, 2015, 5 pages.
Philip, G. et al. (1994). "The human nasal response to capsaicin," J Allergy Clin Immunol 94:1035-1045.
Written Opinion received for PCT Patent Application No. PCT/US2015/57019, mailed on Feb. 11, 2016, 6 pages.

\* cited by examiner

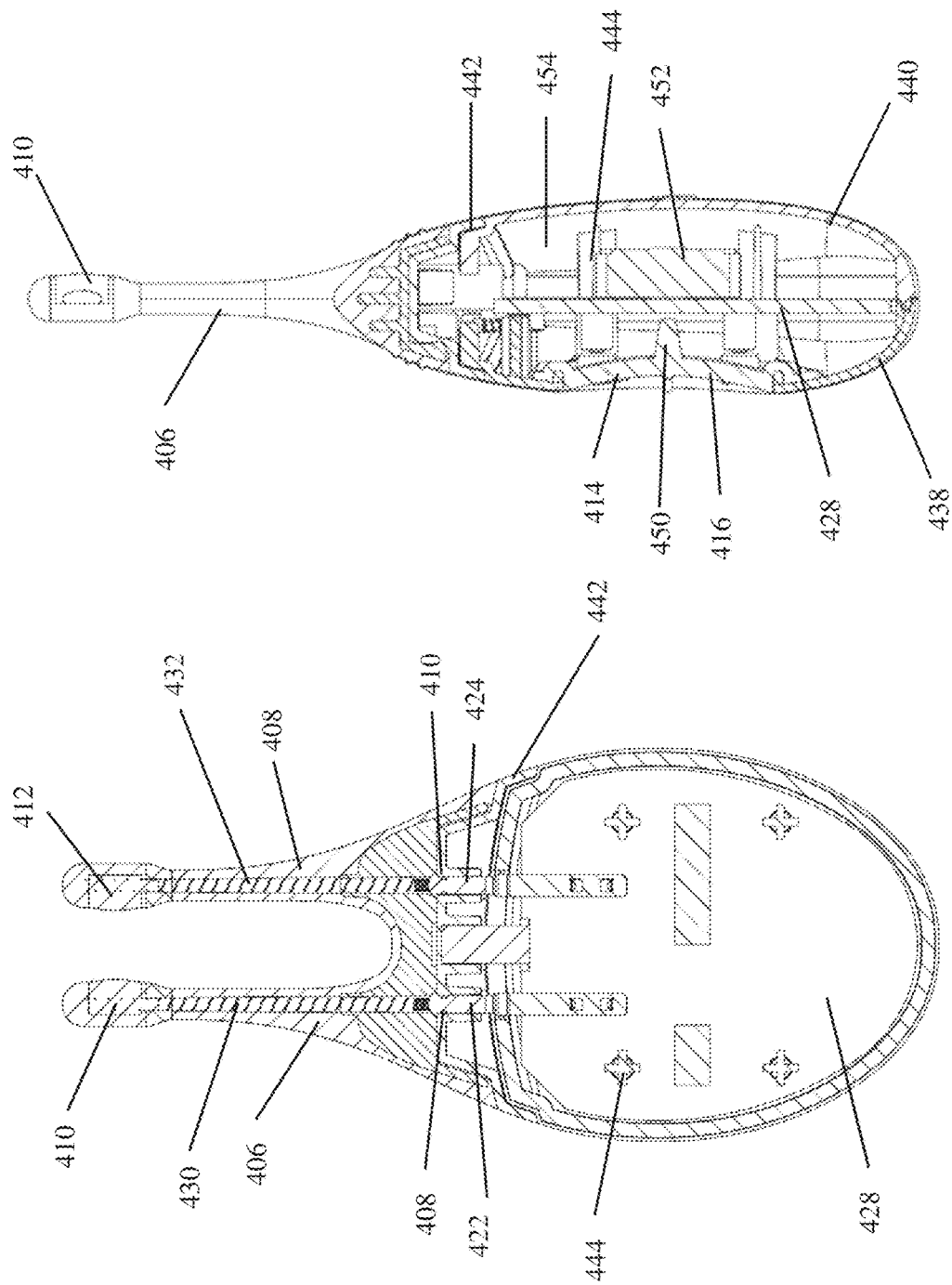

STIMULATION PATTERNS FOR TREATING DRY EYE

CROSS-REFERENCE TO RELATED APPLICATIONS

This application claims priority to U.S. Provisional Patent Application No. 62/029,362, filed on Jul. 25, 2014, and titled "Stimulation Patterns," and to U.S. Provisional Patent Application No. 62/067,416, filed on Oct. 22, 2014, and titled "Stimulation Patterns," both of which are incorporated by reference herein in their entirety.

FIELD

Described herein are electrical stimulation patterns and methods of use thereof for treating dry eye disease or tiredness of the eye. The methods generally include applying patterned stimulation to an anatomical structure located in an ocular region or a nasal region. The electrical stimulation may elicit a reflex that activates the lacrimal gland or directly activate the lacrimal gland or nerves innervating the lacrimal gland to produce tears.

BACKGROUND

Dry Eye Disease ("DED") is a condition that affects millions of people worldwide. More than 40 million people in North America have some form of dry eye, and many millions more suffer worldwide. DED results from the disruption of the natural tear film on the surface of the eye, and can result in ocular discomfort, visual disturbance, and a reduction in vision-related quality of life. Activities of daily living such as driving, computer use, housework, and reading have also been shown to be negatively impacted by DED. Patients with severe cases of DED are at risk for serious ocular health deficiencies such as corneal ulceration and can experience a quality of life deficiency comparable to that of moderate-severe angina.

DED is progressive in nature, and generally results from insufficient tear coverage on the surface of the eye. This poor tear coverage prevents healthy gas exchange and nutrient transport for the ocular surface, promotes cellular desiccation, and creates a poor refractive surface for vision. Poor tear coverage typically results from: 1) insufficient aqueous tear production from the lacrimal glands (e.g., secondary to post-menopausal hormonal deficiency, auto-immune disease, LASIK surgery, etc.), and/or 2) excessive evaporation of aqueous tear resulting from dysfunction of the meibomian glands. In turn, low tear volume causes a hyperosmolar environment that induces inflammation of the ocular surface. This inflammatory response induces apoptosis of surface cells, which in turn prevents proper distribution of the tear film on the ocular surface so that any given tear volume is rendered less effective. A vicious cycle is initiated where more inflammation can ensue and cause further surface cell damage, etc. Additionally, the neural control loop, which controls reflex tear activation, is disrupted because the sensory neurons in the surface of the eye are damaged. As a result, fewer tears are secreted and a second vicious cycle develops that results in further progression of the disease (fewer tears cause nerve cell loss, which results in fewer tears, etc.).

There is a wide spectrum of treatments for DED, however, none provides adequate treatment of the condition. Treatment options include: artificial tear substitutes, ointments, gels, warm compresses, environmental modification, topical cyclosporine, omega-3 fatty acid supplements, punctal plugs, and moisture chamber goggles. Patients with severe disease may further be treated with punctal cautery, systemic cholinergic agonists, systemic anti-inflammatory agents, mucolytic agents, autologous serum tears, PROSE scleral contact lenses, and tarsorrhaphy. Despite these treatment options, DED continues to be considered one of the most poorly treated diseases in ophthalmology. Accordingly, it would be desirable to have a more effective treatment for dry eye.

SUMMARY

Described here are methods for treating one or more conditions (such as dry eye, tired eyes, reducing discomfort from wearing contact lenses, etc.) by providing electrical stimulation to an anatomical structure located in an ocular region or a nasal region. Exemplary anatomical structures include nerves, muscles, mucosal tissues, cutaneous sensory structures such as Parcian corpuscles, Merkel cells, etc., within these regions. The electrical stimulation, when delivered to certain targets as described herein, is generally capable of initiating a reflex circuit that activates the lacrimal gland to produce tears. The reflex circuit may include stimulation of a nerve directly or a cutaneous sensory cell that in turn activates a nerve which then produces either sensory input to the brain, or motor input to a nerve that activates a muscle near, e.g., the eye, which in turn provides sensory input to the brain and initiation of the reflex to activate the lacrimal gland. The electrical stimulation may additionally or alternatively be capable, when delivered to other certain targets as described herein, of directly driving efferent fibers innervating the lacrimal gland to produce tears.

More specifically, methods of generating lacrimation (tear production) by modifying parameters of electrical waveforms to generate afferent or efferent input are described. These methods generally optimize waveforms for a sensed paresthesia, e.g., a sensation of tickle, twitch, and/or vibration in the eyelid and/or vicinity of the eyelid, eyebrow, as well as the temporal and frontal area of the head. Experimentation by the inventors has found that these sensations are strongly associated with lacrimation.

Using the patterned stimulation waveforms disclosed herein, it is believed that sensory nerves are activated to send input to the brain to produce lacrimation. Additionally or alternatively, the patterned stimulation waveforms may activate motor nerves that cause muscles in the vicinity of the orbit, the nose, the mouth, and/or the frontal or temporal face to vibrate in order to generate the sensation of tingle or twitch or vibration as the effect, which initiates the reflex pathway and thereby leads to lacrimation.

The electrical stimulation applied to the anatomical structures generally includes a plurality of waveform parameters that define a patterned waveform. Delivery of the electrical stimulus may help to treat DED by inducing an increase in lacrimation, and may generate a paresthesia sensed by a patient. These patterned waveforms may be capable of increasing tear output as well as patient comfort during and/or after application of the stimulation.

Implantable or hand-held devices may be employed when applying the electrical stimulation. In some variations, the devices may comprise a stimulator body and a stimulator probe, where the stimulator probe comprises one or more nasal insertion prongs, and wherein the stimulator body comprises a control subsystem to control a stimulus to be delivered to the patient via the stimulator probe. In some of these variations, the stimulator probe comprises at least two nasal insertion prongs. In some of these variations, the stimulator probe comprises at least one electrode. In other variations, the electrode comprises one or more of platinum, platinum-iridium, gold, or stainless steel. In some variations, the stimulus is a biphasic pulse waveform. In some of these variations, the biphasic pulse waveform is symmetrical. In some of these variations, the frequency of the biphasic pulse waveform is between 30 Hz and 80 Hz. In some variations, the stimulator probe is releasably connected to the stimulator body. In some variations, the stimulator body is reusable and the stimulator probe is disposable. In some variations, the device further comprises a user interface. In some of these variations, the user interface comprises one or more operating mechanisms to adjust one or more parameters of the stimulus. Additionally or alternatively, the user interface may comprise one or more feedback elements.

In other variations, the devices may include an implantable microstimulator and an external controller. Exemplary implantable devices that may be used to apply the electrical stimulation described herein are disclosed in U.S. patent application Ser. No. 13/441,806, filed Apr. 6, 2012, and titled "Stimulation Devices and Methods," which is hereby incorporated by reference in its entirety. Exemplary hand-held devices, as well as additional exemplary implantable devices, that may be used to apply the electrical stimulation described herein are disclosed in U.S. patent application Ser. No. 14/256,915, filed Apr. 18, 2014, and titled "Nasal Stimulation Devices and Methods," which is hereby incorporated by reference in its entirety.

In general, the methods disclosed herein include applying patterned electrical stimulation to an anatomical structure in an ocular region or a nasal region to activate the lacrimal gland, where the patterned electrical stimulation is defined by a plurality of waveform parameters, and increasing tear production using the patterned electrical stimulation. In some instances, the method further includes confirming activation of the lacrimal gland by evaluating a paresthesia sensed in the ocular region or the nasal region.

The anatomical structure that is stimulated may be a nerve, cutaneous sensory cells (Parcian corpuscles, Merkel cells etc.), muscle, or tissue such as mucosa or sub-mucosa, in the ocular region or nasal region. For example, the anatomical structure may be the nasociliary nerve, the anterior or posterior ethmoid nerve, or the infra-trochlear nerve. In some variations, the anatomical structure is a muscle in the ocular region or the nasal region. In some variations, the anatomical structure comprises a mucosal or sub-mucosal surface in the ocular region or the nasal region. In some instances, the anatomical structure may be cutaneous sensory cells in the nasal or ocular glabrous skin, which naturally sense mechanical input such as pressure, vibration, tingle, temperature, or pain.

As further disclosed herein, the plurality of waveform parameters that define the stimulation waveforms may be selected from the group consisting of on/off duration, frequency, pulse width, amplitude, and shape. Other suitable waveform parameters may also be used. For example, charge injection, which can be calculated by multiplying amplitude and pulse width, may be used as a waveform parameter. In some variations, the plurality of waveform parameters are selected from the group consisting of on/off duration, frequency, pulse width, amplitude, and shape. In some of these variations, the on/off duration ranges from about 0.1 to 5.0 seconds on, and about 0.1 to 5.0 seconds off. In some of these variations, the on/off duration is 1.0 second on, and 1.0 second off. In some of these variations, the on/off duration is 5.0 seconds on, and 5.0 seconds off. In some of these variations, the frequency ranges from about 10 to 200 Hz. In some of these variations, the frequency ranges from about 30 to 150 Hz. In some of these variations, the frequency ranges from about 50 to 80 Hz. In some variations, the frequency is 30 Hz. In some variations, the frequency is 70 Hz. In some variations, the amplitude ranges from about 0.1 to 10 mA. In some of these variations, the maximum amplitude ranges from about 1 to 3 mA. In some variations, the pulse width and amplitude generate a waveform having a triangular, rectangular, or square shape. In some variations, the electrical stimulation is continuously applied. In other variations, the electrical stimulation has on and off periods.

The combination of waveform parameters specific to a particular stimulation waveform, where at least one of the waveform parameters is modulated over time, are referred to herein as "patterns" and the resulting stimulation waveform a "patterned waveform" or "patterned stimulation waveform." The stimulation waveform optimized for a particular patient to activate the lacrimal gland to produce tears and elicit a paresthesia in that patient is referred to herein as a "patient-optimized waveform."

The patterned electrical stimulation may also be applied using a stimulator comprising a plurality of patterned stimulation waveforms stored in memory. Selection of the patterned stimulation from the plurality of stored patterned stimulation waveforms may be random. The patterned stimulation waveforms may also be patient-optimized waveforms.

Systems for generating and applying the electrical stimulation waveforms are further disclosed herein. The systems may generally include one or more stimulation electrodes and a controller, wherein the controller comprises a programmable memory configured to store a plurality of patterned stimulation waveforms. The stimulation waveforms may or may not be associated with a sensed paresthesia. The controller may also be configured to execute a program that cycles through a plurality of waveform parameter options. A user interface may be included and configured in a manner that allows the patient to select one or more of the stored plurality of patterned waveforms.

In some variations, the one or more stimulation electrodes are configured for implantation in an ocular region or a nasal region. In some of these variations, the one or more stimulation electrodes are configured for placement on a mucosal surface or within sub-mucosal tissue. The one or more stimulation electrodes may also be configured for placement within a nasal cavity or a sinus cavity. In other variations, the controller is configured for placement external to the ocular region or the nasal region. In some variations, the patterned electrical stimulation is applied by an electrode device disposed within a nasal cavity or a sinus cavity. In some variations, the patterned electrical stimulation is applied by an electrode device implanted near the lacrimal gland. In some of variations, the systems are configured for activating cutaneous sensors or nerve fibers innervating cutaneous sensors in the mucosal surface or within sub-mucosal tissue. In some variations, the systems are configured for activating cutaneous sensors or nerve fibers innervating cutaneous sensors in tissue such as skin and muscles of the ocular region, the forehead or the temple area of the head.

In some variations, the patterned electrical stimulation is applied by an electrode device comprising a plurality of patterned stimulation waveforms stored in memory. In some of these variations, the applied patterned stimulation is randomly selected from the plurality of stored patterned stimulation waveforms. In some of these variations, the plurality of stored patterned stimulation waveforms are patient-optimized waveforms. In some variations, the applied patterned stimulation is stored in memory as a patient-optimized waveform.

In some variations the systems described herein comprise one or more stimulation electrodes and a controller, wherein the controller comprises a programmable memory configured to store a plurality of patterned stimulation waveforms associated with a sensed paresthesia. In some variations, the one or more stimulation electrodes are configured for implantation in an ocular region or a nasal region. In some of these variations, the controller is configured for placement external to the ocular region or the nasal region. In some variations, the one or more stimulation electrodes are configured for placement on a mucosal surface or within sub-mucosal tissue. In some variations, the one or more stimulation electrodes are configured for placement within a nasal cavity or a sinus cavity.

In some variations, the programmable memory is capable of storing up to 10 patterned stimulation waveforms. In some variations the system further comprising a user interface for selecting one or more of the stored plurality of patterned waveforms. In some variations, the controller is configured to execute a program that cycles through a plurality of waveform parameter options.

In some variations the methods described herein comprise applying patterned electrical stimulation to an anatomical structure in an ocular region or a nasal region to activate the lacrimal gland, and increasing tear production using the patterned electrical stimulation, wherein the patterned electrical stimulation comprises a biphasic waveform having cathodic and anodic pulse pairs, each pulse having a duration and amplitude, wherein the ratio of duration to amplitude for each pulse is variable over time. In some variations, the biphasic waveform is charge balanced. In some of these variations, the ratio of duration to amplitude for the cathodic pulse varies over time according to a function having a phase of increase according to an exponential function and a phase of decrease according to an exponential function. In some of these variations, the ratio of duration to amplitude for the cathodic pulse varies over time according to a sawtooth function. In some of these variations, the ratio of duration to amplitude for the cathodic pulse varies over time according to a sinusoidal function.

In some variations the methods described herein comprise applying patterned electrical stimulation to an anatomical structure in an ocular region or a nasal region to activate the lacrimal gland, and increasing tear production using the patterned electrical stimulation, wherein the patterned electrical stimulation comprises a biphasic waveform having cathodic and anodic pulse pairs, wherein a subset of the pulse pairs have a leading cathodic pulse and a subset of the pulse pairs have a leading anodic pulse.

The frequency, peak-to-peak amplitude, and pulse width of the waveforms may be constant, but in some variations the stimulator may be configured to vary the frequency, amplitude, and/or pulse width of the waveform. This variation may occur according to a pre-determined plan, or may be configured to occur randomly within given parameters. For example, in some variations the waveform may be configured such that the peak-to-peak amplitude of the waveform varies over time (e.g., according to a sinusoidal function having a beat frequency, a sawtoothed function, or an exponential function); in some variations the waveform may be configured such that the frequency of the waveform varies over time (e.g., according to a sinusoidal function, a sawtoothed function, or an exponential function); or in some variations the waveform may be configured such that the pulse width of the waveform varies over time (e.g., according to a sinusoidal function, a sawtoothed function, or an exponential function). In some variations, rectangular stimulation pulses of a variable fundamental frequency are employed. In other variations, triangular stimulation pulses may be used and modulated as described for rectangular stimulation pulses.

In some variations, the methods described herein comprise a method for inducing lacrimation. In some variations the method comprises delivering an electrical stimulus to a patient having dry eye, wherein the electrical stimulus is delivered from a handheld stimulator, and wherein the electrical stimulus comprises a waveform having a pulse width that varies during delivery. In some variations the method comprises delivering an electrical stimulus to a patient having dry eye using a handheld stimulator, wherein the electrical stimulus can be one of a plurality of preset waveforms comprising at least a first preset waveform and a second preset waveform, and changing the electrical stimulus from the first preset waveform to the second preset waveform while delivering the electrical stimulus. The electrical stimulus may be changed from the first preset waveform to the second preset waveform by the patient.

In some variations, the methods described herein comprise providing a device to a patient having dry eye, wherein the device is configured to deliver a plurality of electrical waveforms to an anatomical target in a patient, and instructing the patient to select one or more of the plurality of waveforms based on an amount of sensed paresthesia felt during delivery of the waveform. In some of these variations, the anatomical target may be the nasal mucosa. In some of these variations, the anatomical target may be the anterior ethmoidal nerve. In others of these variations, the anatomical target may be in an ocular region. In some of these variations, at least one of the plurality of waveforms may have a pulse width that varies over time. In some of these variations, the pulse width may vary over time according to an exponential function.

In some variations, the devices described herein comprise a handheld stimulator comprising a stimulator body comprising a user interface, and a stimulator probe comprising a nasal insertion prong comprising an electrode. The stimulator may be configured to deliver a plurality of electrical waveforms, and the user interface may be configured for selection of one of the plurality of electrical waveforms. Each of the waveforms may have at least one of a pulse shape, maximum amplitude, pulse width, or frequency that is modulated over time. In some of these variations, each of the waveforms has at least two of a pulse shape, maximum amplitude, pulse width, or frequency that is modulated over time. In some variations, each of the waveforms has a pulse shape that is modulated over time. In some variations, the waveform comprises a first period comprising a two-phase current-controlled waveform, and a second period comprising a current-controlled phase followed by a voltage-controlled phase.

BRIEF DESCRIPTION OF THE DRAWINGS

FIGS. 4A-4C depict an exemplary handheld stimulator.

DETAILED DESCRIPTION

Described herein are devices, systems, and methods for treating one or more conditions (such as dry eye, tired eyes, ocular discomfort from wearing contact lenses, etc.) by providing electrical stimulation to an anatomical structure located in an ocular region or a nasal region. Specifically, the methods disclosed herein generally include applying patterned electrical stimulation to an anatomical structure in an ocular region or a nasal region to activate the lacrimal gland, where the patterned electrical stimulation is defined by a plurality of waveform parameters. The electrical stimulation may result in effects such as increased tear production during or after delivery of the stimulus.

Figure 1:
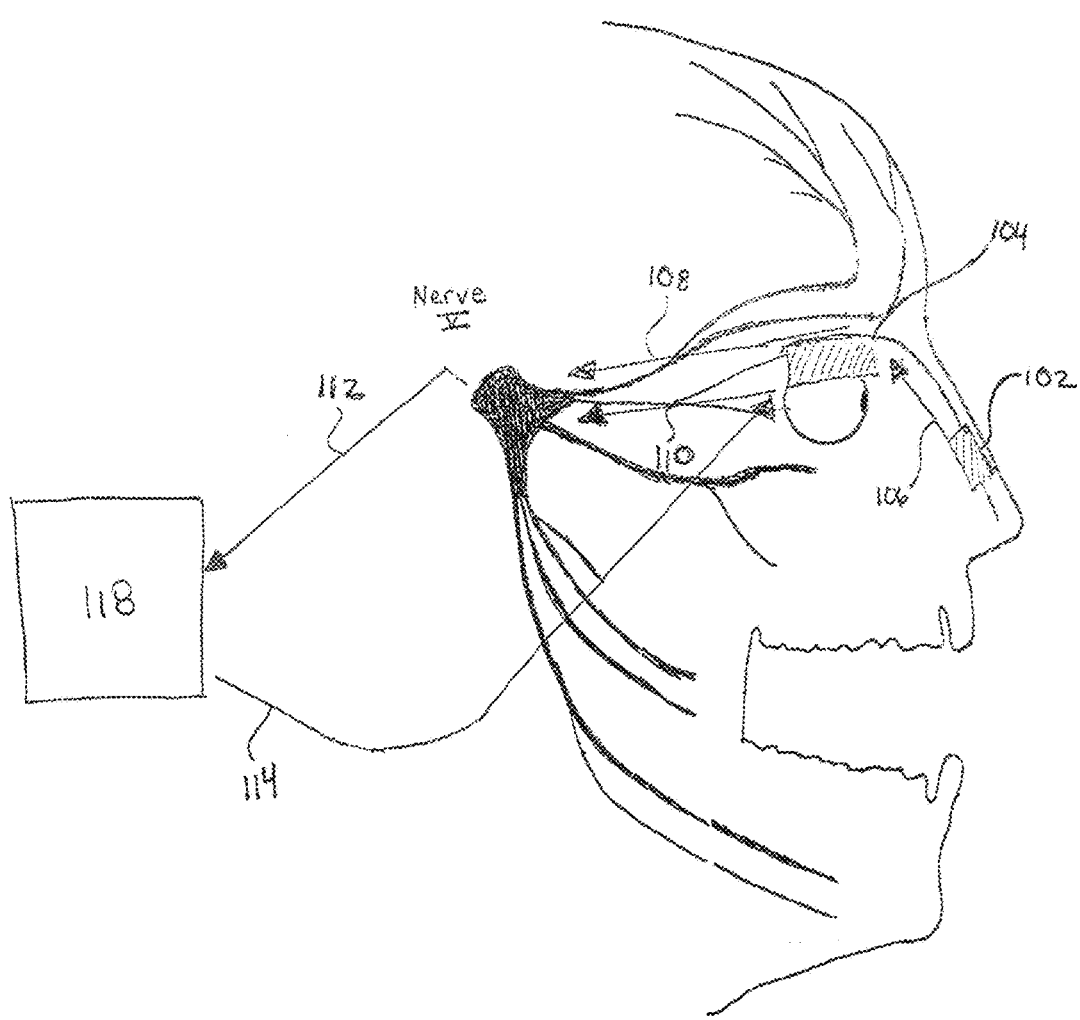
FIG. 1 illustrates a proposed pathway of action of sensory output processed in various ganglia of the peripheral nervous system and nuclei of the central nervous system.

In general, the methods disclosed herein include electrically stimulating nerves, muscles (thus indirectly nerves via muscle spindles and golgi-tendon receptors providing sensory information back to the central nervous system), and/or glands in the orbit of the eye or the nasal mucosa and sub-mucosa. With that approach, neural tissue may be activated in some manner. For example, referring to FIG. 1, the inventors hypothesize that the activation at an intra-nasal location 102 or at an ocular location 104 causes action potentials to run antidromically and orthodromically from the activation point if the electrode is activating the nerves directly, and orthodromically on afferent nerves if glands and muscles are activated to cause sensory input to the brain. Sensory input to the brain reaches the lacrimal nucleus in the pons, after passing several ganglia on the way, as shown by arrows 106, 108, 110, and 112. Here it is likely that neural computation and data reduction happens in each of the ganglia as well as in the nuclei in the pons before the information is further relayed to areas of the sensory cortex in the cerebrum. Accordingly, the activation of neural tissue, directly or indirectly, may cause circuitry in the central nervous system (e.g., brain, spinal cord, potentially the ganglia in the peripheral nervous system (PNS)) to respond to the input. Output from the brainstem 118 may then send feedback, as shown by arrow 114, to the lacrimal gland.

The inventors found that some patients report that, after initially noticing a stimulation input, they do not feel the stimulation after a few (e.g., less than 30) seconds, even though the stimulation continued to be delivered. The assessment was that the central nervous system must have performed data reduction and thus facilitated accommodation in these patients. Thus, the approach here is aimed at providing patients with stimulation paradigms that reduced patient accommodation.

Exemplary Stimulators

The stimulation waveforms described herein may be delivered via implanted or non-implanted (e.g., handheld) stimulators.

Exemplary Implantable Microstimulators

Figure 2A:
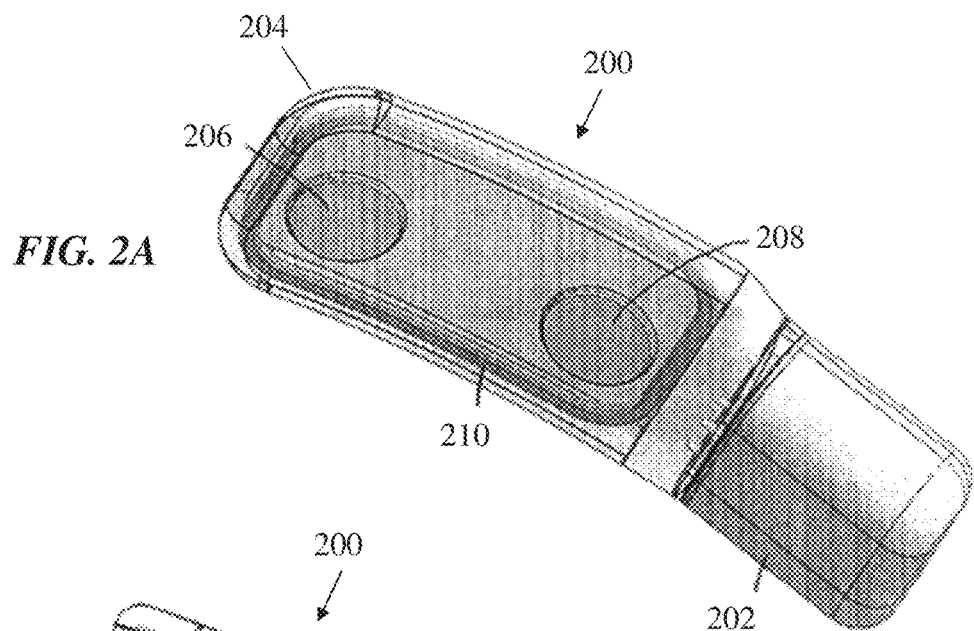
FIGS. 2A-2C depict an exemplary implantable microstimulator.
Figure 2B:
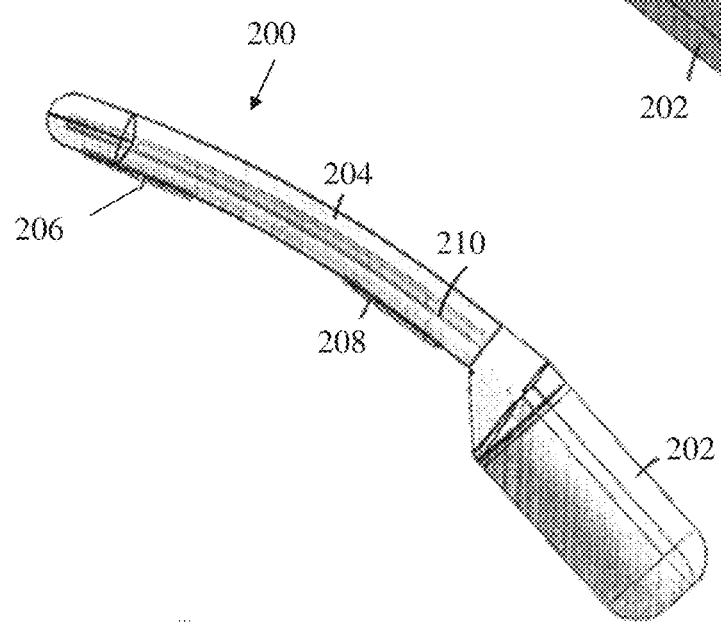
Figure 2C:
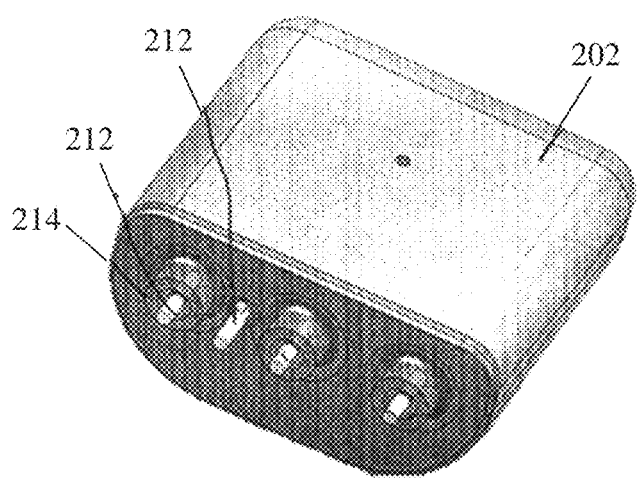

When the stimulation waveforms described herein are applied using an implantable stimulator, the stimulator may comprise a microstimulator comprising a housing and a corresponding and complementary flexible extension connected to the housing, forming a unitary microstimulator. An example is shown in FIGS. 2A-2C. As shown there, the microstimulator 200 may comprise a housing 202 and a flexible extension 204 connected to the housing 202. The housing 202 may be hermetically sealed, and may contain some or all of the stimulation circuitry therein. The microstimulator 200 may comprise any stimulation circuits, such as those described in U.S. patent application Ser. No. 13/441,806, which was previously incorporated by reference in its entirety. The housing 202 may be formed from one or more metals (e.g., titanium) or other biocompatible materials.

The extension 204 may be formed from a flexible material such as silicon, and may comprise a first electrode 206, a second electrode 208, and a coil 210. In some variations, the extension 204 may be a molded component, such as molded silicon. The extension may have a corresponding and complementary shape to the housing, such that the extension and housing together have a unitary shape, as shown in FIGS. 2A-2B. The flexible extension 204 may conform to one or more portions of the anatomy (e.g., the orbit or the lacrimal gland) when implanted in tissue. FIG. 2B shows a side view of the microstimulator 200. As shown there, the thickness of the extension 204 may be less than that of the housing 202, and may increase to the thickness of housing 202. Additionally, the width of the extension 204 is shown in FIG. 2A as being greater than the width of the housing 202, and may decrease to the thickness of the housing 202.

The electrodes 206 and 208 and coil 210 may be connected to the microstimulator circuitry via one or more feedthroughs. For example, FIG. 2C shows a perspective view of the housing 202 with the extension 204 removed. As shown there, housing 202 may comprise a plurality of feedthroughs 212 that extend through the housing 202. One or more elements (e.g., one of the electrodes 206 or 208 or the coil 210) may be electrically connected to the hermetically-sealed stimulation circuitry by connection to the feedthroughs 212. Additionally, some of the feedthroughs 212 may comprise an insulating member 214 which may electrically isolate the feedthrough 212 from the housing 202. This and other implantable stimulators that may deliver the electrical stimuli described herein are described in U.S. patent application Ser. No. 13/441,806, was previously incorporated by reference in its entirety; and in U.S. patent application Ser. No. 14/256,915, which was previously incorporated by reference in its entirety.

When the stimulator is an implantable microstimulator, the system may further comprise a controller, which may communicate with the microstimulator to transmit and/or receive power, information, or the like. For example, in variations in which a stimulation system comprises a microstimulator having a passive stimulation circuit (or a stimulation circuit that does not otherwise include a battery or internal power supply), the controller signal may power the stimulator via the output signal of the controller. The controller may communicate with the microstimulator wirelessly and/or via a wired connection. The controller may be configured for implantation within the body, or may be configured to remain external to the body. The controller may be disposable, may be reusable, or may be partially reusable. In some instances, the controller may be rechargeable.

Figure 3:
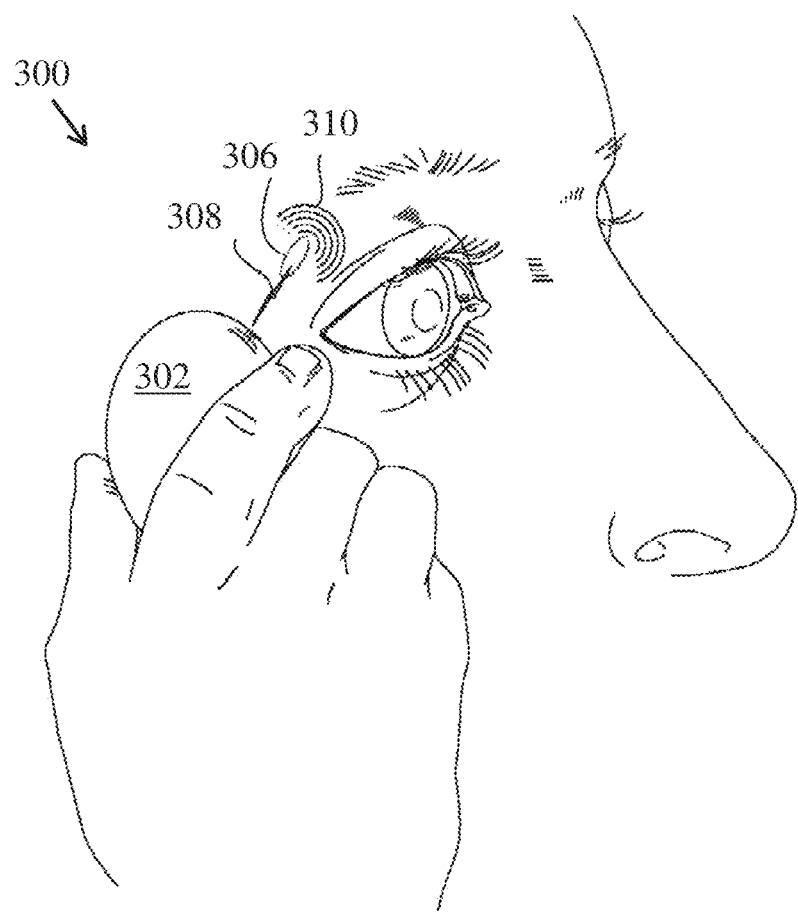
FIG. 3 depicts an exemplary external controller for an implantable micro stimulator.

FIG. 3 depicts an exemplary external controller. As shown there, a stimulation system 300 includes a controller 302 comprising a hand-held device. The controller 302 may be brought into the vicinity of an implanted microstimulator 306, and may produce an output signal 308 received by the implanted microstimulator 306. The implanted microstimulator may in turn generate a stimulation signal 310 used to stimulate an anatomical target, as described in more detail herein. This and other controllers that may be used to deliver the electrical stimuli described herein are described in U.S. patent application Ser. No. 13/441,806, which was previously incorporated by reference in its entirety.

The length and width of the microstimulator may be selected to permit placement of a portion of the microstimulator on, partially within or about the lacrimal gland, or adjacent to a desired tissue, such as the lacrimal gland or a nerve desired to be stimulated, such as but not limited to the nasociliary nerve or anterior ethmoidal nerve, as described in more detail in U.S. patent application Ser. No. 13/441, 806, was previously incorporated by reference in its entirety; in U.S. patent application Ser. No. 14/256,915, which was previously incorporated by reference in its entirety; and in U.S. patent application Ser. No. 14/207,072, filed Mar. 12, 2014, and titled "Implant Delivery Devices, Systems, and Methods," and which is hereby incorporated by reference in its entirety.

The microstimulator may be injectable into a patient using a delivery system. The delivery system may comprise an insertion device (such as conduit, a shaft to which the microstimulator is removably attachable, or the like) and/or a dissection tool. In some variations, the insertion device is a 12 or larger gauge needle. In other variations, the insertion device comprises a cannula. In some variations, the insertion device may comprise a piston assembly, which in some variations may be spring-powered. The microstimulator may be loaded into the insertion device, and the insertion device may be inserted into an insertion pathway. In some variations in which the microstimulator is implanted into an ocular region, using an anatomical landmark at the corner of the eye, a delivery device (e.g., a needle) may be positioned in proximity to the lacrimal gland, and the microstimulator may be deployed using the delivery device. Anatomical landmarks include, but are not limited to, the lateral canthis, an eyelid margin, a palpebral lobe of the lacrimal gland, the orbital rim, a bony protuberance on the superior-lateral aspect of the orbit, the vascular bed, or the like. In some variations, a microstimulator may be implanted by lifting the eyelid, forming an insertion pathway through the conjunctiva under the eyelid, and advancing the microstimulator into the insertion pathway. The insertion pathway may be formed using a dissection tool. In some variations, the insertion pathway may be formed using a dissection element of an insertion tool. In some variations, the insertion pathway may be formed between the periosteum and the orbital bone. In other variations, the insertion pathway may be formed between the periosteum and the lacrimal gland. The micro stimulator may have one or more features to facilitate minimally invasive retrieval. U.S. patent application Ser. No. 14/207,072, which was previously incorporated by reference in its entirely, describes other variations of insertion devices that may be used to implant microstimulators described herein.

Exemplary Handheld Stimulators

Figure 4A:
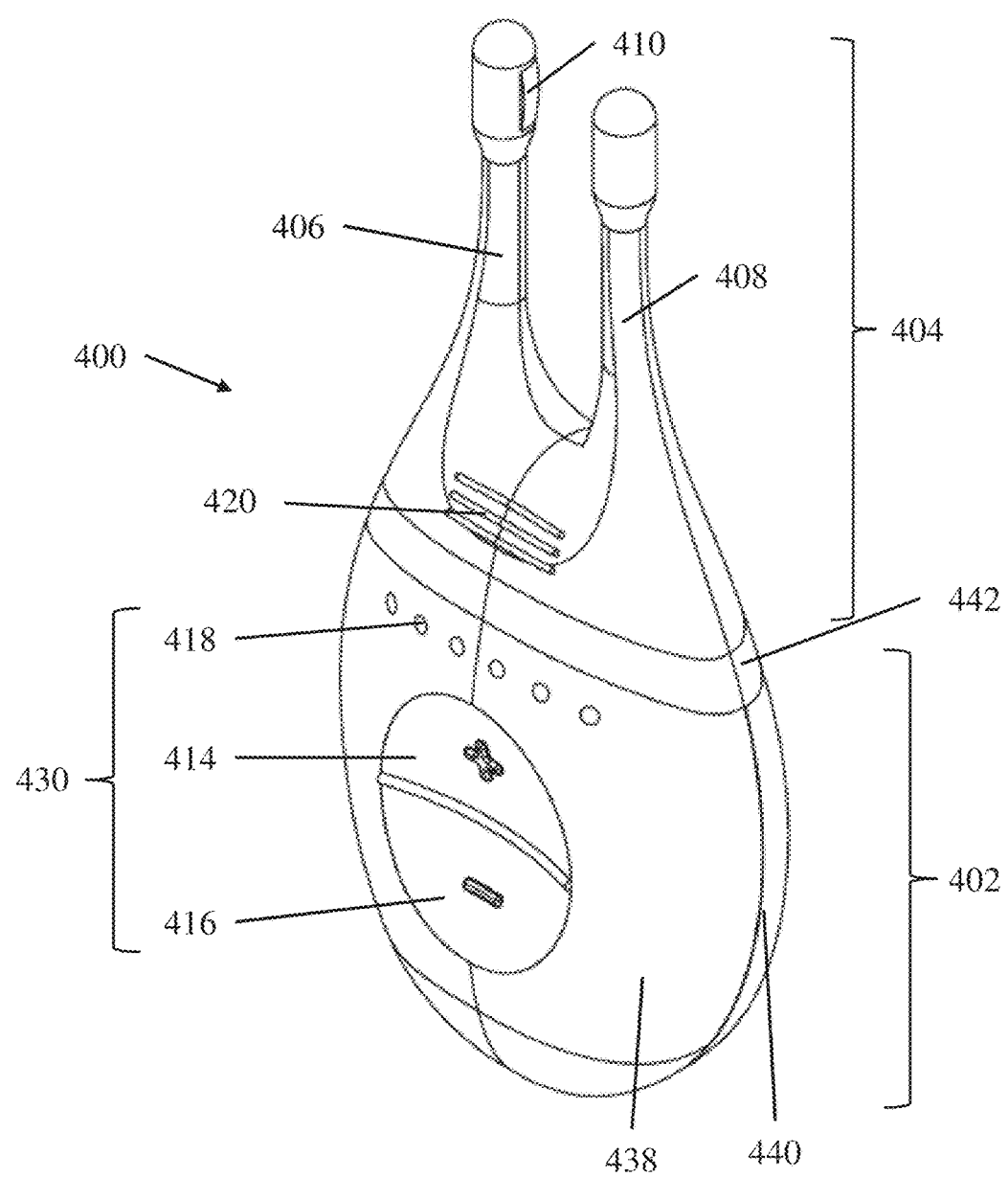

FIGS. 4A-4C show perspective, cut-away back, and cut-away side views, respectively, of an illustrative variation of a handheld stimulator 400, respectively. As shown in FIGS. 4A-4C, the stimulator 400 may comprise a stimulator body 402 and a stimulator probe 404. Generally, the stimulator body 402 may be configured to generate a stimulus, described in more detail herein, that may be delivered to the patient. The stimulator body 402 may comprise a front housing 438, back housing 440, and proximal housing 442, which may fit together to define a body cavity 454. The body cavity 454 may contain a control subsystem 436 and a power source 452, which together may generate and control the stimulus.

The stimulus may be delivered to a patient via the stimulator probe 404. In some variations the stimulator body 402 and stimulator probe 404 may be reversibly attachable. Some or all of the stimulator 400 may be disposable, and some or all of the stimulator 400 may be reusable. For example, in variations where the stimulator probe 404 is releasably connected to the stimulator body 402, the stimulator body 402 may be reusable, and the stimulator probe 404 may be disposable and periodically replaced. In some of these variations, the device comprises a disabling mechanism that prevents stimulus delivery to the patient when the stimulator probe is reconnected to the stimulator body after being disconnected from the stimulator body. Additionally or alternatively, the device may comprise a lockout mechanism that prevents the stimulator probe from being reconnected to the stimulator body after being disconnected from the stimulator body. In some variations, the device further comprises a detachable protective cap.

The stimulator probe may comprise at least one nasal insertion prong, which may be configured to be at least partially inserted into the nasal cavity of a patient. In the handheld stimulator variation shown in FIGS. 4A-4C, the stimulator probe 404 may comprise two nasal insertion prongs 406 and 408. The nasal insertion prongs may be self-aligning when inserted into the nostrils of the patient. The stimulator probe 404 may further comprise ridges 420, which may allow the patient to more easily grip the probe 404.

Each nasal insertion prong may comprise at least one electrode. As shown in FIGS. 4A-4C, the probe 404 may comprise a first electrode 410 on nasal insertion prong 406 and a second electrode 412 on nasal insertion prong 408. As shown in the cut-away view of the stimulator 400 in FIG. 4B, the electrodes 410 and 412 may be connected to leads 430 and 432 located within prongs 406 and 408, respectively. The leads 430 and 432 may in turn be connected to connectors 422 and 424, respectively. Connectors 422 and 424 may extend through lumens 408 and 410 in the proximal housing 442, and may connect directly or indirectly to the control subsystem 436 and power source 452. As such, the electrical stimulus may travel from the control subsystem 436 through the connectors 422 and 424, through the leads 430 and 432, and through the electrodes 410 and 412. In some variations, the electrode comprises a hydrogel, which is described in more detail in U.S. patent application Ser. No. 14/630,471, filed Feb. 24, 2015, and titled "Polymer Formulation for Nasolacrimal Stimulation," which is hereby incorporated by reference in its entirety.

The stimulator body may comprise a user interface comprising one or more operating mechanisms to adjust one or more parameters of the stimulus, as described in more detail below. The operating mechanisms may provide information to the control subsystem, which may comprise a processor, memory, and/or stimulation subsystem. In some variations, the operating mechanisms may comprise first and second buttons, as illustrated for example in FIGS. 4A and 4C as 414 and 416. In some variations, pressing the first button may turn on the stimulator and/or change the stimulus waveform, while pressing the second button 416 may turn off the stimulator and/or change the stimulus waveform. Additionally or alternatively, the user interface may comprise one or more feedback elements (e.g., based on light, sound, vibration, or the like). As shown, the user feedback elements may comprise light-based indicators, shown in the variation of FIG. 4A as indicators 418, which may provide information to the user. This stimulator and other hand-held stimulators that may deliver the electrical stimuli described herein are described in U.S. patent application Ser. No. 14/256,915, which was previously incorporated by reference in its entirety.

Waveforms

The electrical stimulation waveforms delivered by the stimulators described herein may be tailored for specific treatment regimens and/or specific patients. It should be appreciated that the waveforms described here may be delivered via a multi-polar, such as bipolar, tripolar, quad-polar, or higher-polar configuration or a monopolar configuration with distal return. The waveforms may be a sinusoidal, quasi-sinusoidal, square-wave, sawtooth, ramped, or triangular waveforms, truncated-versions thereof (e.g., where the waveform plateaus when a certain amplitude is reached), or the like.

As is described in more detail herein, when patterning of electrical stimulation waveforms is employed, waveform parameters such as the shape, the frequency, the amplitude, and the pulse width may be modulated. The frequency, pulse-width, and/or amplitude of the waveform may be modulated linearly, exponentially, as a sawtooth, a sinusoidal form, etc., or they may be modulated randomly. The stimulation can also be interrupted as part of the patterning. That is, the stimulation can be in an on/off condition, e.g., for durations of 1 second on/1 second off, 5 seconds on/5 seconds off, etc. Modulation of the waveform shape (e.g., rectangular vs. triangular vs. exponential) in a rhythmic or non-deterministic, non-rhythmic fashion may also be used. Thus, numerous variations in waveform patterning can be achieved. It should be understood that combinations of these parameter changes over time in a repetitive manner may also be considered patterning. In some instances, random patterning may be employed. Patterning may help to prevent patient habituation to the applied stimulation (i.e., may help to prevent the patient response to the stimulation decreasing during stimulation).

In some instances, it may be desirable to configure the stimulation waveform to minimize side effects. In some instances, it may be desirable to promote stimulation of larger-diameter nerves (e.g., afferent fibers of the trigeminal nerve), which may promote a therapeutic effect, while reducing the stimulation of smaller nerves (e.g., a-delta fibers, c fibers, sympathetic and parasympathetic fibers), which may result in pain, discomfort, or mucus production. Generally, for smaller pulse-widths, the activation threshold for larger-diameter nerves may be lower than the activation threshold for the smaller nerve fibers. Conversely, for larger pulse-widths, the activation threshold for larger-diameter nerves may be higher than the activation threshold for the smaller nerve fibers. Accordingly, in some instances, it may be desirable to select a pulse width that preferably actuates the larger-diameter nerves. In some variations, the pulse width may be between 50 μs and about 1200 μs. As another example, certain waveforms may minimize activation of the branches of the trigeminal nerve (e.g., CN V2) that travel to the teeth. These may include waveforms ranging from 30 μs to 300 μs in pulse width, 10 Hz to 150 Hz in frequency, and 0.1 mA to 5 mA in amplitude.

The stimulation may be delivered periodically at regular or irregular intervals. Stimulation bursts may be delivered periodically at regular or irregular intervals. The stimulation amplitude, pulse width, or frequency may be modified during the course of stimulation. For example, the stimulation amplitude may be ramped from a low amplitude to a higher amplitude over a period of time. In other variations, the stimulation amplitude may be ramped from a high amplitude to a lower amplitude over a period of time. The stimulation pulse width may also be ramped from a low pulse width to a higher pulse width over a period of time. The stimulation pulse width may be ramped from a high pulse width to a lower pulse width over a period of time. The ramp period may be between 1 second and 15 minutes. Alternatively, the ramp period may be between 5 seconds and 30 seconds.

The patterned stimulation waveforms described herein may be used to increase the comfort of the patient and/or may be used to improve the efficacy of the stimulation, and thus, described below are waveform parameters that may be used alone or in combination to increase comfort and/or efficacy.

Shape

In some instances, the waveform shape or modulation thereof may affect the comfort and/or efficacy of the stimulation. When the stimulator (electrode device) is configured to create a pulse-based electrical waveform, the pulses may be any suitable pulses (e.g., a square pulse, a haversine pulse, or the like). The pulses delivered by these waveforms may by biphasic, alternating monophasic, or monophasic, or the like. When a pulse is biphasic, the pulse may include a pair of single phase portions having opposite polarities (e.g., a first phase and a charge-balancing phase having an opposite polarity of the first phase). Each phase of the biphasic pulse may be either voltage-controlled or current-controlled. In some variations, both the first phase and the charge-balancing phase of the biphasic pulse may be current-controlled. In other variations, both the first phase and the charge-balancing phase of the biphasic pulse may be voltage-controlled. In still other variations, the first phase of the biphasic pulse may be current-controlled, and the second phase of the biphasic pulse may be voltage-controlled, or vice-versa. In some instances, a combination of current-controlled bilateral stimulation and voltage-controlled charge balancing may allow for unilateral stimulation, and by modifying the waveform shape, may allow for switching between areas of stimulation, e.g., between nostrils when electrodes are located in each nostril, as described herein.

In some variations in which the waveform comprises a biphasic pulse, it may be desirable to configure the biphasic pulse to be charge-balanced, so that the net charge delivered by the biphasic pulse is approximately zero. In some variations, a biphasic pulse may be symmetric, such that the first phase and the charge-balancing phase have the same pulse width and amplitude. Having a symmetric biphasic pulse may allow the same type of stimulus to be delivered, e.g., to each nasal cavity. The pulses of a first phase may stimulate a first side of the nose (while providing a charge-balancing phase to a second side of the nose), while the pulses of the opposite phase may stimulate the second side of the nose (while providing a charge-balancing phase to the first side of the nose).

In other variations in which the waveform comprises a biphasic pulse, a biphasic pulse may be asymmetric, where the amplitude and/or pulse width of the first pulse may differ from that of the charge-balancing phase. Even if the biphasic pulse is asymmetric, the biphasic pulse may be charge-balanced. For example, the cathodic pulse may have lower amplitude but longer duration than the anodic pulse, or the cathodic pulse may have higher amplitude but shorter duration than the anodic pulse. In both instances, the charge injection (amplitude times duration) may be equal for each pulse, such that the net charge delivered by the biphasic pulse is approximately zero.

Figure 5A:
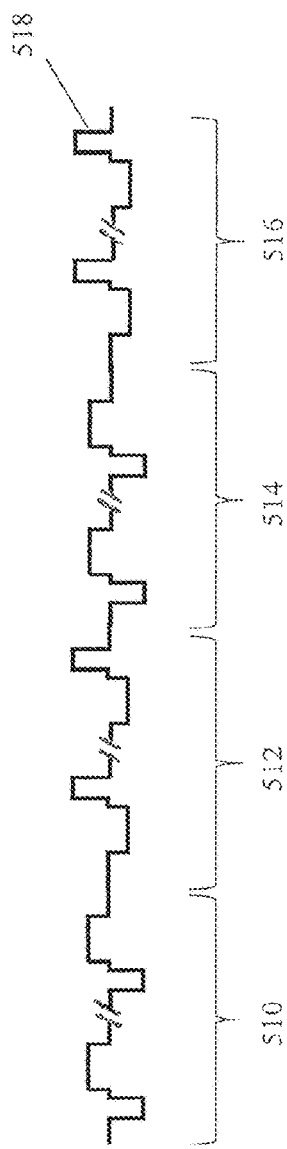
FIGS. 5A-5C show exemplary waveforms.
Figure 5B:
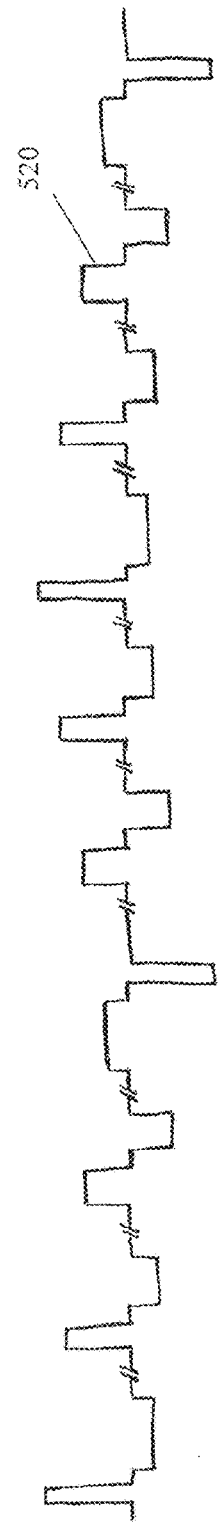
Figure 5C:
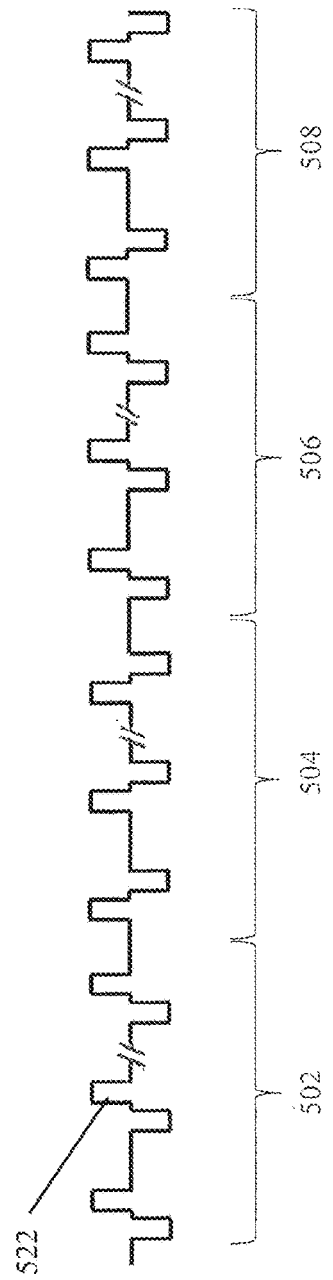

The shape of the waveform may be changed to preferentially activate the tissue near an electrode. For example, FIGS. 5A-5C illustrate exemplary waveforms configured to preferentially activate tissue near one of two electrodes, and where the preferential activation may move from near one electrode to the other over time. In variations in which the stimulator is a handheld stimulator configured to have an electrode in each nostril, for example, this preferential activation may allow for preferential activation of tissue in one of the two nostrils, which may change over time. For example, FIG. 5A shows a variation of a biphasic charge-balanced waveform 518 in which the aspect ratios (amplitude:duration) of the pulses changes over time. Shown there is a waveform that has a first pattern wherein a leading cathodic pulse has a greater amplitude and shorter duration in comparison to the following anodic pulse. This pattern is found in the time periods indicated by 510 and 514. The waveform has a second pattern where the leading cathodic pulse has a lesser amplitude and longer duration in comparison to the following anodic pulse. This pattern is found in the time periods indicated by 512 and 516. It should be appreciated that each time period may have any suitable duration and thus comprise any suitable number of pulses. As one example, each time period may last for about 1 second. In other examples, each time period may last for less than 1 second, about 1 to about 5 seconds, about 5 to about 10 seconds, about 10 to about 20 seconds, or longer.

In some variations the waveform may transition between two aspect ratios in an abrupt fashion. In other variations the transition may be gradual, where the aspect ratio of the cathodic pulse may increase over time and then decrease over time, while the aspect ratio of the anodic pulse may decrease over time and then increase over time. FIG. 5B shows an example of a waveform 520 that gradually transitions between aspect ratios. These increases and decreases may have any suitable form, such as linear increases and decreases or sinusoidal increases and decreases. In other variations, the transition may have a sawtooth shape, in which the aspect ratio of the cathodic pulse increases gradually over time while the aspect ratio of the anodic pulse decreases gradually over time, and then the aspect ratio of the cathodic pulse decreases abruptly while the aspect ratio of the anodic pulse increases abruptly.

In some variations, the polarity is switched back and forth between a pattern in which the cathodic pulse is first and a pattern in which the anodic pulse is first. For example, FIG. 5C shows an illustrative version of such a stimulation waveform 522. As shown there, the time periods indicated by 502 and 506 may have a cathodic pulse and then an anodic pulse, while the time periods indicated by 504 and 508 may have an anodic pulse and then a cathodic pulse. It should be appreciated that each time period may have any suitable duration. As one example, each time period may last for about 1 second. In other examples, each time period may last for less than 1 second, about 1-5 seconds, about 5-10 seconds, about 10-20 seconds, or longer. In some variations, each time period may last for a single pair of pulses, such that the stimulation waveform comprises a repeating pattern of two anodic pulses and two cathodic pulses.

Although the patterns having variable amplitude:duration aspect ratios may have uniform charge injection, they may preferentially activate the tissue near one of the two electrodes. That is, when the leading cathodic pulse has a greater amplitude and shorter duration than the anodic pulse, the waveform may preferentially activate tissue near a cathodic electrode; when the leading cathodic pulse has a lesser amplitude and longer duration than the anodic pulse, the waveform may preferentially activate tissue near an anodic electrode. Changing aspect ratios and switching polarities as described herein may increase the lacrimation response. This may be because switching polarities leads to non-linear addition of the stimuli as perceived by the central nervous system, as well as because switching polarities reduces a patient's accommodation to the stimuli.

Frequency

In order to treat dry eye or otherwise produce a tearing response by stimulating tissue, the stimulators described herein may be configured to generate one of more waveforms at frequencies suitable for stimulating targeted tissue (e.g., a nerve). The frequency may affect the comfort and/or efficacy of the stimulation. Generally, the frequency is preferably between about 0.1 Hz and about 200 Hz. In some of these variations, the frequency is preferably between about 10 Hz and about 200 Hz. In some of these variations, the frequency is preferably between about 30 Hz and about 150 Hz. In others of these variations, the frequency is preferably between about 50 Hz and about 80 Hz. In others of these variations, the frequency is preferably between about 30 Hz and about 60 Hz. In some variations, the frequency may be about 1.5 Hz, about 10.25 Hz, about 70 Hz, about 150 Hz, about 25 Hz, about 27.5 Hz, about 30 Hz, about 32.5 Hz, about 35 Hz, about 37.5 Hz, about 40 Hz, about 42.5 Hz, about 45 Hz, about 47.5 Hz, about 50 Hz, about 52.5 Hz, about 55 Hz, about 57.5 Hz, about 60 Hz, about 62.5 Hz, or about 65 Hz. In some variations, high frequencies, such as those between about 145 Hz and about 155 Hz may be too high for each pulse to stimulate/activate the target tissues. As a result, the stimulation may be interpreted by the patient to have an element of randomness, which in turn may help to reduce patient habituation. The frequencies described herein may be suitable for stimulating the targeted tissue to initiate a reflex circuit that activates the lacrimal gland to produce tears, and/or suitable for directly driving efferent fibers innervating the lacrimal gland. In some instances, the frequency may be chosen for preferential activation of certain anatomical targets, as described herein.

Amplitude

In order to treat dry eye or otherwise produce a tearing response by stimulating tissue, the stimulators described herein may be configured to deliver a current suitable for stimulating targeted tissue (e.g., a nerve). The maximum amplitude or modulation thereof may affect the comfort and/or efficacy of the stimulation. When the stimulus comprises a biphasic pulse and the first phase of the biphasic pulse is current-controlled, the first phase may preferably have an amplitude between about 1.0 mA and about 10 mA. Amplitudes within these ranges may be high enough to stimulate targeted tissue, but sufficiently low as to avoid any significant heating of tissue, ablation of tissue, or the like. In some variations the amplitude may be between about 1.0 mA and about 5.0 mA. In other variations, the first phase may have an amplitude of about 0.1 mA, about 0.2 mA, about 0.3 mA, about 0.4 mA, about 0.5 mA, about 0.6 mA, about 0.7 mA, about 0.8 mA, about 0.9 mA, or about 1.0 mA. In some variations, the amplitude may be variable. For example, the amplitude may vary between about 1.3 mA and about 1.5 mA, about 2.2 mA and about 2.5 mA, about 3.2 mA and about 3.7 mA, about 4.3 mA and about 5.0 mA. When the first phase of a biphasic pulse is voltage-controlled, the first phase may preferably have an amplitude between about 10 mV and about 100 V.

Figure 6A:
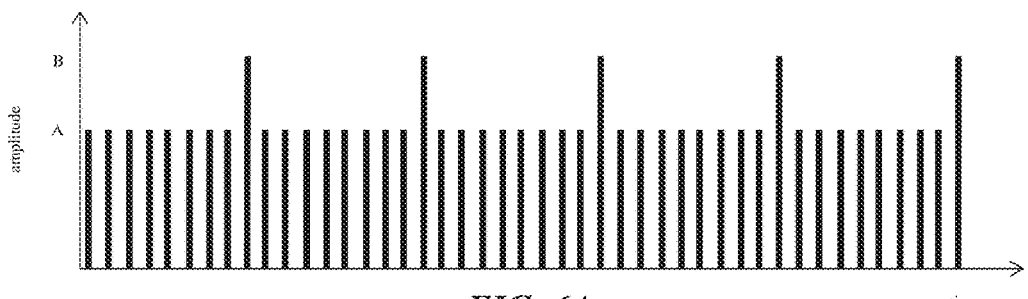
FIGS. 6A-6D illustrate exemplary amplitude variations over time.
Figure 6B:
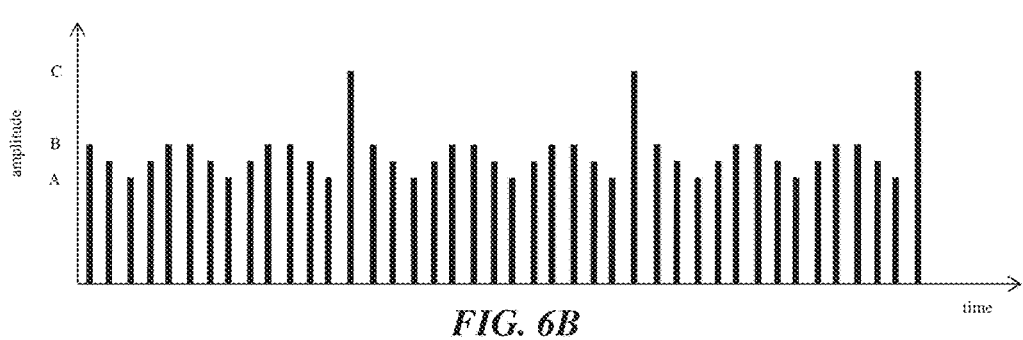
Figure 6C:
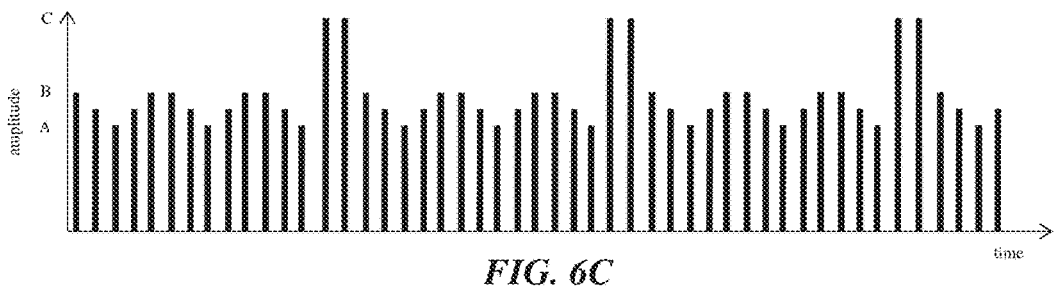
Figure 6D:
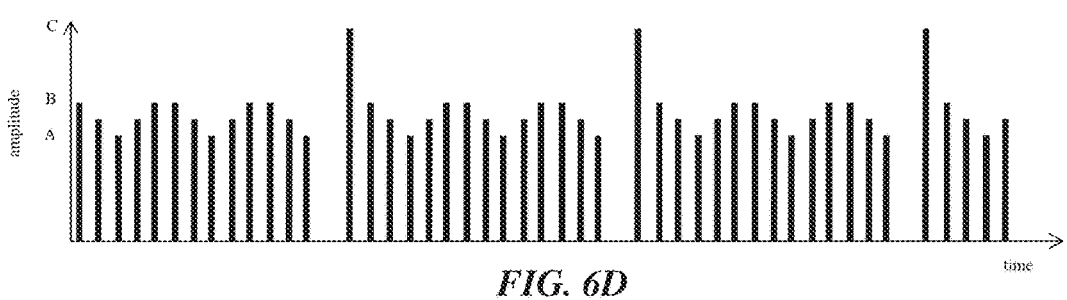

When a stimulator is configured to deliver a pulse-based waveform, in some variations, the amplitude of the pulses may be constant over time. In other variations, the amplitude of the pulses may vary over time. This may reduce patient accommodation. In some variations, the amplitude of pulses may increase (linearly, exponentially, etc.) from a minimum value to a maximum value, drop to the minimum value, and repeat as necessary. In some variations, the amplitude of the pulses may vary according to a sinusoidal profile. In another variation, as illustrated in FIG. 6A, the amplitude may periodically increase from a baseline amplitude (A) to a higher amplitude (B) for a single pulse. In yet another variation, as illustrated in FIGS. 6B-6C, the amplitude of the pulses may follow a periodically increasing and decreasing pattern between two lower amplitudes (A, B), and periodically increase to a higher amplitude (C) for a single pulse (FIG. 6B) or for a plurality of pulses (e.g., two pulses) (FIG. 6C). In yet another variation, as illustrated in FIG. 6D, a higher amplitude pulse (or pulses) may be preceded by a brief pause (i.e., no current delivery). Each of these types of amplitude modulation may be implemented alone or in combination with any other type of amplitude modulation, and may reduce patient accommodation.

In some variations in which the amplitude varies over time, the amplitude may vary at a frequency suitable for reducing patient accommodation or increasing patient comfort such as between about 0.1 Hz and about 5 Hz, between about 1 Hz and about 5 Hz, between about 1 Hz and 2 Hz, between about 2 Hz and 3 Hz, between about 3 Hz and 4 Hz, or about 4 Hz and about 5 Hz. In some variation, the amplitude may vary at a frequency of about 1.0 Hz, about 1.1 Hz, about 1.2 Hz, about 1.3 Hz, about 1.4 Hz, about 1.5 Hz, about 1.6 Hz, about 1.7 Hz, about 1.8 Hz, about 1.9 Hz, about 2.0 Hz, about 2.1 Hz, about 2.2 Hz, about 2.3 Hz, about 2.4 Hz, about 2.5 Hz, about 2.6 Hz, about 2.7 Hz, about 2.8 Hz, about 2.9 Hz, about 3.0 Hz, about 3.1 Hz, about 3.2 Hz, about 3.3 Hz about 3.4 Hz, about 3.5 Hz, about 3.6 Hz, about 3.7 Hz, about 3.8 Hz, about 3.9 Hz, or about 4.0 Hz. In other variations, the stimulation waveform may be a modulated high frequency signal (e.g., sinusoidal), which may be modulated at a beat frequency of the ranges described above. In such variations, the carrier frequency may be between about 100 Hz and about 100 kHz.

Pulse Width

In order to treat dry eye or otherwise produce a tearing response by stimulating tissue, the stimulators described herein may be configured to deliver a waveform in which the first phase may preferably have a pulse width between about 1 μs and about 10 ms. In some of these variations, the pulse width may be between about 10 μs and about 100 μs. In other variations, the pulse width may be between about 100 μs and about 1 ms. In yet other variations, the pulse width may be between about 0 μs and about 300 μs. In yet other variations, the pulse width may be between about 0 μs and 500 μs. As described above, it may be desirable to select a pulse width that preferably actuates larger-diameter nerves. In some variations, the pulse width may be between 50 μs and about 1200 μs. As another example, pulse widths of 30 μs to 300 μs may minimize activation of the branches of the trigeminal nerve (e.g., CN V2) that travel to the teeth.

Figure 7A:
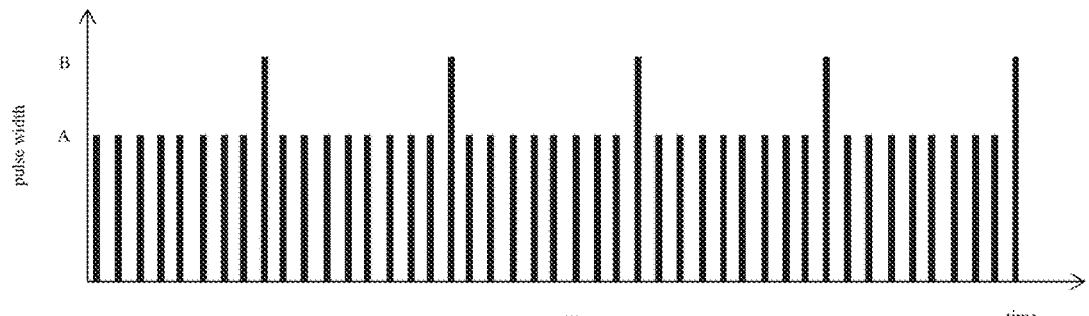
FIGS. 7A-7D illustrate exemplary pulse width variations over time.
Figure 7B:
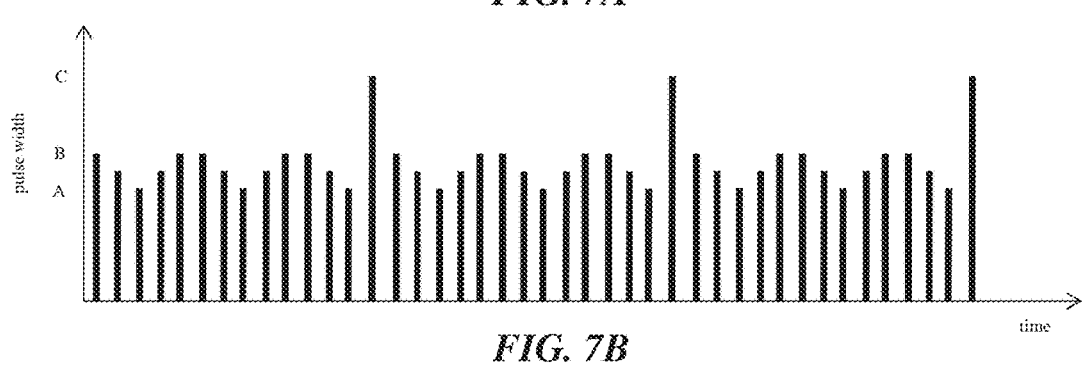
Figure 7C:
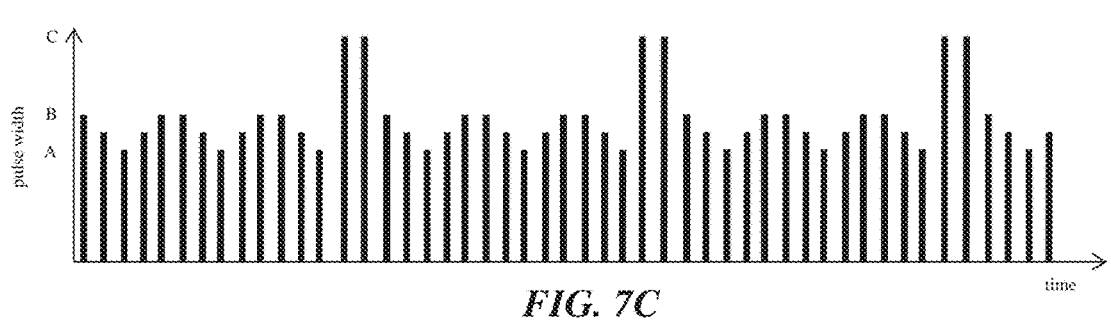
Figure 7D:
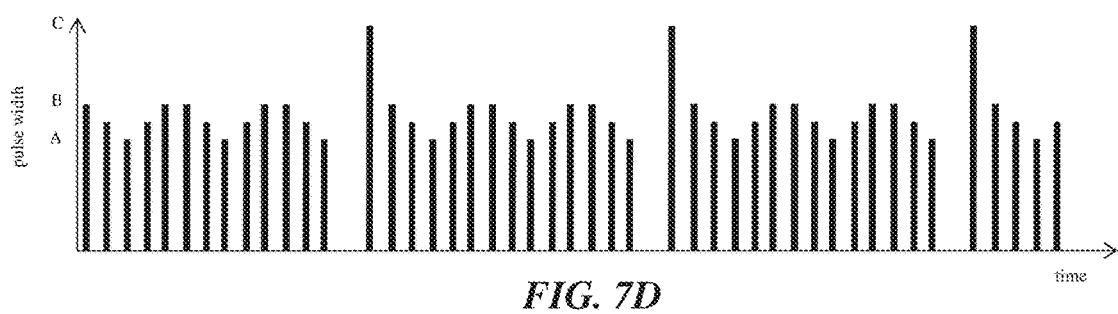

In some variations, the amplitude of the pulses may be constant over time. In other variations, the pulse width may vary over time. Pulse width modulation over time may increase the efficacy and/or comfort of the stimulation. In some variations, the pulse width may increase (linearly, exponentially, etc.) from a minimum value to a maximum value, drop to the minimum value, and repeat as necessary. In some variations, the pulse width may vary according to a sinusoidal profile. In another variation, as illustrated in FIG. 7A, the pulse width may periodically increase from a baseline pulse width (A) to a longer pulse width (B) for a single pulse. In yet another variation, as illustrated in FIGS. 7B-7C, the pulse width may follow a periodically increasing and decreasing pattern between two shorter pulse widths (A, B), and periodically lengthen to a longer pulse width (C) for a single pulse (FIG. 7B) or for a plurality of pulses (e.g., two pulses) (FIG. 7C). In yet another variation, as illustrated in FIG. 7D, a longer pulse width pulse (or pulses) may be preceded by a brief pause (i.e., no current delivery). Each of these types of pulse width modulation may be implemented alone or in combination with any other type of pulse width modulation. In any form of pulse width modulation, the pulse width may vary at any suitable frequency. In some variations the pulse width may vary at about 0.1 Hz, about 0.2 Hz, about 0.3 Hz, about 0.4 Hz, about 0.5 Hz, about 0.6 Hz, about 0.7 Hz, about 0.8 Hz, about 0.9 Hz, about 1 Hz, about 1.1 Hz, about 1.2 Hz, about 1.3 Hz, about 1.4 Hz, or about 1.5 Hz. In some variations, modulation of the pulse width at a rate between about 0.5 Hz and 1 Hz may be desirable to increase patient comfort during stimulation.

In some variations, the increase and decrease of pulse width may be defined by a function implemented by the stimulator. For example, the pulse width may be defined by a function such that the pulse width varies exponentially. In one variation, the function defining pulse width may comprise two phases—a first phase during which the pulse width of the leading pulse increases over time, and a second phase during which the pulse width of the leading pulse decreases over time. During the first phase, the pulse width of the leading pulse approaches the maximum pulse width according to an exponential function, where at time t, PW{t} is defined by the equation $$PW\{t\} = (PW_{max} - PW_{min})\left(1 - e^{-\left(\frac{t}{\tau}\right)}\right)$$

where $PW_{max}$ is the maximum allowed pulse width, $PW_{min}$ is the minimum allowed pulse width, and $\tau$ is a time constant.

Once a predetermined amount of time has elapsed (a multiple of time constant $\tau$), the pulse width modulation may enter the second phase. During the second phase, the pulse width of the leading pulse exponentially decays from its maximum value to a minimum value following the exponential equation $$PW\{t\} = (PW_{max} - PW_{min})\left(e^{-\left(\frac{t}{\tau}\right)}\right).$$

Figure 8:
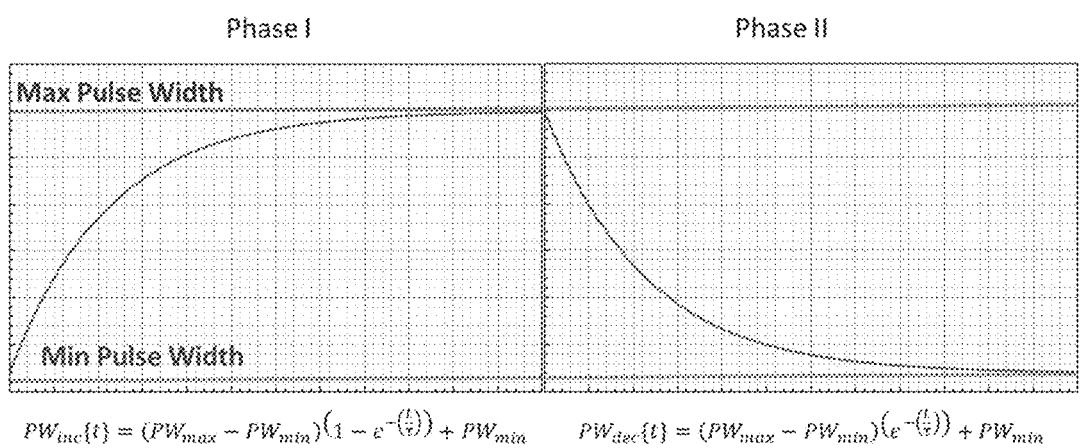
FIG. 8 shows an exemplary function defining pulse widths increasing and decaying according to an exponential function.

After a predetermined amount of time has elapsed (a multiple of time constant $\tau$), the pulse width modulation may re-enter the first phase, and the cycle may repeat. The pulse width of the secondary (charge balancing) pulse is increased and decreased accordingly to retain charge full balancing. $PW_{max}$, $PW_{min}$, and $\tau$ may have any suitable values to achieve the pulse widths described herein, but in one example the waveform may have a $PW_{max}$ of 300 μs, $PW_{min}$ of 0 μs, and $\tau$ of 1/3 μs. In other variations, for example, $PW_{max}$, may be about 100 μs, about 200 μs, about 300 μs, about 400 μs, or about 500 μs; $PW_{min}$ may be about 0 μs, about 10 μs, about 50 μs, or about 100 μs; and $\tau$ may be about 1/3 μs, about 1/4 μs, about 1/5 μs, or about 1/6 μs. An exemplary function defining exponentially increasing and decaying pulse widths is shown in FIG. 8.

On/Off Periods

In some instances, the waveforms described herein may be delivered in a continuous fashion, while in other instances, the waveforms may be delivered in a non-continuous fashion having on periods and off periods, which may reduce patient accommodation. Exemplary on/off durations include without limitation, 1 second on/1 second off, 1 second on/2 seconds off, 2 seconds on/1 seconds off, 5 seconds on/5 seconds off, 0.2 seconds on/0.8 seconds off, less than 1 second on/less than 10 seconds off.

Exemplary Waveforms

It should be appreciated any of the above waveform parameters and variations in parameters may be combined to generate a patterned waveform as described herein, and these waveforms may be delivered by any of the stimulators described herein. For example, in variations where the waveform comprises a biphasic pulse, the biphasic pulse may have any suitable frequencies, pulse widths, and amplitudes. The stimulation amplitude, pulse width, and frequency may be the same from pulse to pulse, or may vary over time, as described in more detail herein. Combinations of these parameters may increase the efficacy and/or comfort of stimulation, and in some cases, the efficacy and/or comfort may differ by individual patient, as described in more detail herein. Exemplary patterned waveform parameters categorized by device type are listed below in Table 1.

TABLE 1

Exemplary Waveform Parameters

| | | Waveform Parameters | | | |
|---|---|---|---|---|---|
| Device Type | Stimulation Target | On/Off | Frequency (Hz) | Pulse Width (PW) | Amplitude (mA) |
| Ocular Stimulator (implantable) | Orbital nerves (afferent & efferent) | Constant on | 30 | Fixed from 50 μs to 1200 μs | 0.1 to 10 |
| | | 1 sec on/ 1 sec off | 30 | | |
| | | 5 sec on/ 5 sec off | 30 | | |
| | | 1 sec on/ 1 sec off | 70 | | |
| | | 1 sec on/ 1 sec off | 155 | | |
| | | Constant on | Modulated from 30 to 70 in triangular fashion | | |
| | | Constant on | 30 | Triangular modulated from 50 μs to max PW at 0.5 Hz | |
| | | Constant on | 30 | Triangular modulated from 50 μs to max PW at 1 Hz | |
| | | Constant on | 70 | Triangular modulated from 50 μs to max PW at 0.5 Hz | |
| Nasal Stimulator (handheld or implantable) | Internal and external nasal nerves (e.g., anterior ethmoidal nerve) | Constant on | 30 | 0 μs to 300 μs | 0.1 to 10 |
| | | Constant on | 50 | | |
| | | Constant on | 80 | | |
| | | Constant on | 150 | | |
| | | 1 sec on/ 1 sec off | 30 | | |
| | | 1 sec on/ 1 sec off | 50 | | |

TABLE 1-continued

Exemplary Waveform Parameters

| Device Type | Stimulation Target | On/Off | Frequency (Hz) | Pulse Width (PW) | Amplitude (mA) |
|---|---|---|---|---|---|
| | | 1 sec on/ 1 sec off | 80 | | |
| | | Constant on | 30 | | |
| | | 1 sec on/ 1 sec off | 70 | | |

In variations in which a waveform is an alternating monophasic pulsed waveform, each pulse delivered by the stimulator may have a single phase, and successive pulses may have alternating polarities. Generally, the alternating monophasic pulses are delivered in pairs at a given frequency (such as one or more of the frequencies listed above, such as between 30 Hz and 80 Hz), and may have an inter-pulse interval between the first and second pulse of the pair (e.g., about 100 μs, between 50 μs and 150 μs or the like). Each pulse may be current-controlled or voltage-controlled, and consecutive pulses need not be both current-controlled or both voltage-controlled. In some variations where the pulse waveform is charged-balanced, the waveform may comprise a passive charge-balancing phase after delivery of a pair of monophasic pulses, which may allow the waveform to compensate for charge differences between the pulses.

When a stimulator configured to deliver an electrical stimulation waveform is positioned to place an electrode on either side of the nasal septum, alternating monophasic pulses may promote bilateral stimulation of nasal tissue. The pulses of a first phase may stimulate a first side of the nose (while providing a charge-balancing phase to a second side of the nose), while the pulses of the opposite phase may stimulate the second side of the nose (while providing a charge-balancing phase to the first side of the nose), since nerves may respond differently to anodic and cathodic pulses. The inter-pulse interval may give time for the stimulation provided by a first phase pulse to activate/polarize the target nerves prior to being reversed by an opposite phase pulse.

Patient-Optimized Waveforms

Figure 9:
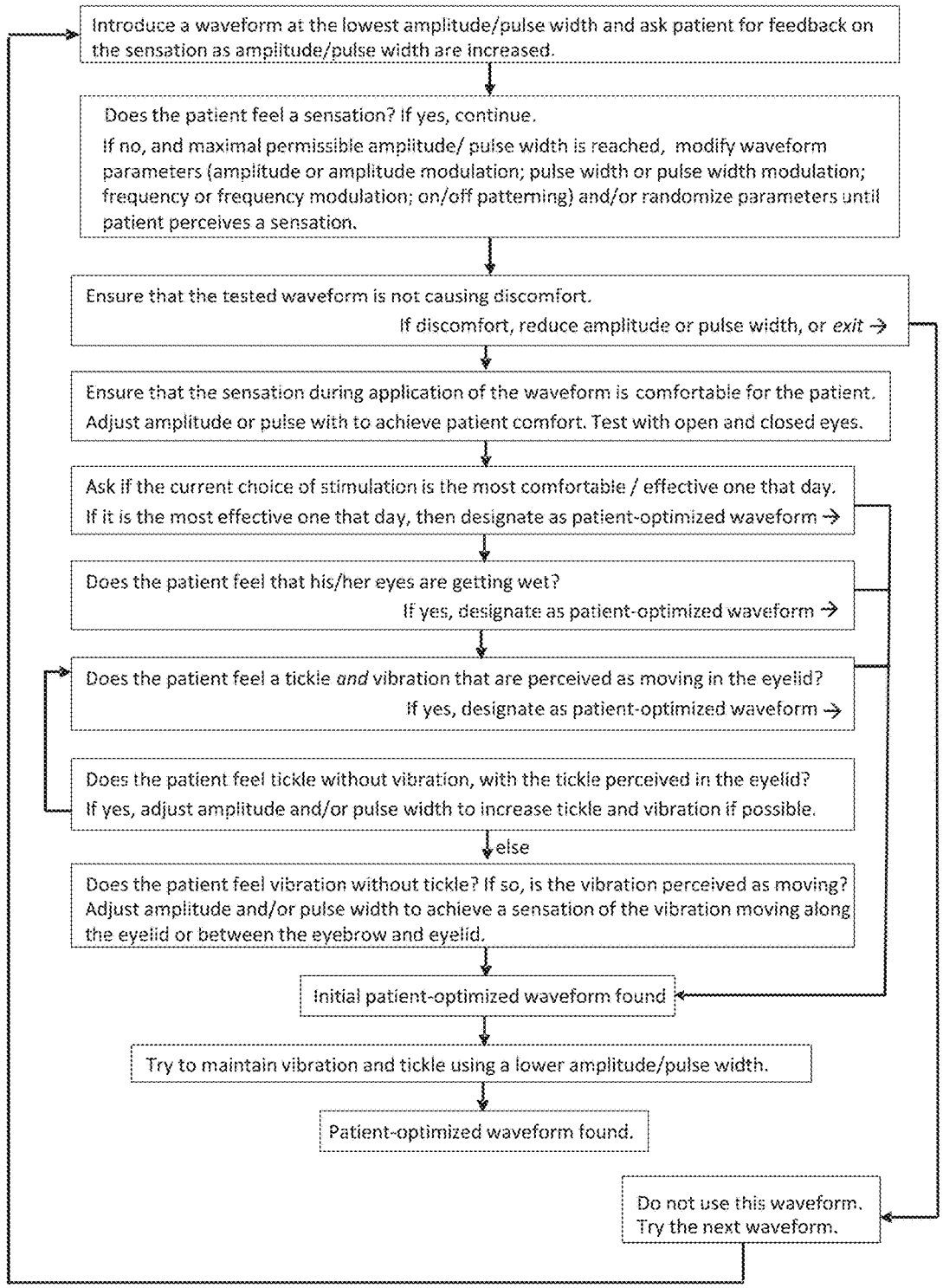
FIG. 9 shows a flowchart illustrating a method used in determining a patient-optimized waveform.

Experimentation by the inventors has found that in some instances, lacrimation caused by stimulation using patterned waveforms may be increased by identification of one or more patient-optimized waveforms for a particular patient, where the patient-optimized waveforms may comprise combinations of the waveform parameters described herein. As such, a method for identification of patient-optimized waveforms is desirable. Experimentation by the inventors has also found that sensed paresthesia is strongly associated with lacrimation, and thus patient perceptions of paresthesia may be used in identification of patient-optimized waveforms. An exemplary method for obtaining patient-optimized waveforms in a patient having a microstimulator implanted in an ocular region is illustrated in FIG. 9. It may be desirable to perform this method for each individual to increase the effectiveness of stimulation (e.g., to increase tearing).

As shown there, a waveform may be assessed to determine if it is a patient-optimized waveform by delivering an electrical stimulus comprising the waveform to the patient using a stimulator described herein. The method may comprise first delivering a waveform at the lowest amplitude and/or pulse width and asking the patient for feedback on the sensation as the amplitude and/or pulse width is increased. The method may then comprise assessing whether the patient feels any sensation during delivery of the electrical stimulus. If not, a different waveform may be selected (e.g., having a different combination of parameters, such as frequency, amplitude, pulse width, on/off period, or the temporal modulation of these parameters). The method may further comprise ensuring that the patient is not experiencing discomfort. If the patient is experiencing discomfort, the method may be restarted with a new waveform, or the amplitude and/or the pulse width may be reduced to alleviate discomfort. Similarly, the method may comprise ensuring that the sensation during application of the waveform is comfortable to the patient. The amplitude and/or pulse width may be adjusted to achieve patient comfort. Comfort may be assessed with the patient's eyes both open and closed.

A waveform may be designated as a patient-optimized waveform if the patient perceives the waveform as the most comfortable and/or effective waveform felt that day; and/or if the patient feels his/her eyes getting wet; and/or if the patient perceives paresthesia—more particularly, if both a tickle and a vibration are perceived as moving in the eyelid. If the patient perceives a tickle in the eyelid but no vibration, the amplitude and/or pulse width may be adjusted to achieve increased perception of tickle and/or vibration. If the patient perceives a vibration but not tickle, the amplitude and/or pulse width may be adjusted to achieve an increased sensation of movement of the vibration (e.g., between the eyelid and eyebrow). It may also be desirable that a patient feels a sensation (e.g., tickle or vibration) after delivery of the stimulus ends. In each case of an identified patient-optimized waveform, a lower amplitude and/or pulse width may be tested to determine whether the same sensation can be achieved using a lower amplitude and/or pulse width.

While the method in FIG. 9 is described with respect to a patient having an implantable stimulator located in an ocular region, it should be appreciated that a similar method may be used to identify one or more patient-optimized waveforms for an implantable stimulator in another region (e.g., a nasal region) or for a handheld stimulator. Once a patient-optimized waveform or waveforms are identified, a stimulator may be configured to deliver the waveform(s). In some variations, an external device may be used to configure the stimulator to deliver the identified waveform(s). In variations in which the system comprises a controller for use with an implantable stimulator having a passive stimulation circuit, a controller configured to generate an output signal that results in the identified stimulation waveform(s) may be used.

Devices Having a Plurality of Waveforms

Some variations of the stimulators described herein may be configured with a plurality of waveforms, such that a clinician and/or patient may select a desired waveform from the plurality of available waveforms. For example, the stimulator may include a plurality of stimulation waveforms saved on a chip. For example, 2, 3, 4, 5, 6, 7, 8, 9, 10, or more than 10 stimulation waveforms may be saved on a chip. In one variation, two to ten stimulation waveforms are saved on a chip. In other variations, two to eight stimulation waveforms, or three to five stimulation waveforms may be saved on the device chip. In some variations, a preferred set of waveforms to be saved on a stimulator may be preselected by a clinician based on initial testing of a variety of stimulation waveforms for a particular patient, such as via the method described above. It may be useful for the saved stimulation waveforms to be those that elicit strong paresthesia in the patient, because experimentation by the inventors has found that sensed paresthesia is more strongly associated with lacrimation, as described herein. In other variations, a stimulator may be preconfigured with a plurality of stimulation waveforms not unique to an individual patient.

In some variations, for every stimulation provided during the day, a different waveform may be randomly selected from the saved plurality of waveforms. By randomly selecting a different waveform each time, the risk of patient developing tolerance to any particular stimulation pattern may be lowered. In another implementation, a multiplexor might be used to provide different combinations of internally saved waveforms to form a "quasi-non-repetitive" waveform when combining pieces from different repetitive waveforms. By multiplexing different waveforms to one combined waveform, habituation to the waveform can potentially be limited further.

In some variations, a patient may be able to selectively choose between the plurality of stimulation waveforms saved on the stimulator, for example, using a user interface such as a user interface as described herein. In variations having such a user interface, the user interface may comprise one or more operating mechanisms, which may allow the user (i.e., the patient) to control the stimulation waveform. For example, the user interface may comprise one or more structures, such as but not limited to a button, slider, lever, touch pad, knob, or deformable/squeezable portion of the housing, which may allow the user to change the stimulation waveform.

The different waveforms may be configured such that a patient may perceive them as spanning a range of intensities. In variations in which the stimulator is configured to deliver waveforms with different shapes, a patient may be able to change the tissue that is preferentially stimulated by the waveform as described herein by selecting a waveform having a different shape (e.g., switching from a waveform having a cathodic pulse first to a waveform having an anodic pulse first). In some variations, when a patient turns on the stimulator for a second or subsequent treatment period, the stimulator may initially turn on to a waveform selected previously by the patient (e.g., the waveform used during the previous treatment session, the most commonly used waveform during a plurality of treatment sessions, etc.).

For example, in the instance where a handheld nasal stimulator is employed, after the user has placed a portion of the stimulator in contact with the nasal tissue, the user may increase the perceived intensity of the stimulus by changing between the plurality of stimulation waveforms. It may be desirable for the patient to increase the intensity of the stimulus until the stimulus causes preferred paresthesia (e.g., tingling, tickling, prickling) without causing discomfort. As such, the patient may be able to self-determine the proper stimulation intensity and self-adjust the stimulus to a waveform effective to achieve the desired result (e.g., tear production). It may be desirable for the user to increase the intensity of the stimulus slowly in order to minimize discomfort. Some patients might prefer their sensation level to change over the course of time. They might want to start with a strong sensation, followed by a weak sensation. They might prefer to start with a weak sensation (e.g., light tickle) followed by a stronger temporary sensation (e.g., light discomfort for a very short time). Some patients may be able to reduce a sensation of needing to sneeze during stimulation if strong and weak sensations are varied.

In one particular example, a stimulator may be configured to deliver a plurality of different waveforms each having a combination of one or more of shape modulation, maximum amplitude modulation, pulse width modulation, and frequency modulation, as described herein. In some instances, the stimulator may be stimulator 400 described above with respect to FIGS. 4A-4C. In other instances, the stimulator may be the microstimulator 200 described above with respect to FIGS. 2A-2C.

Figure 10:
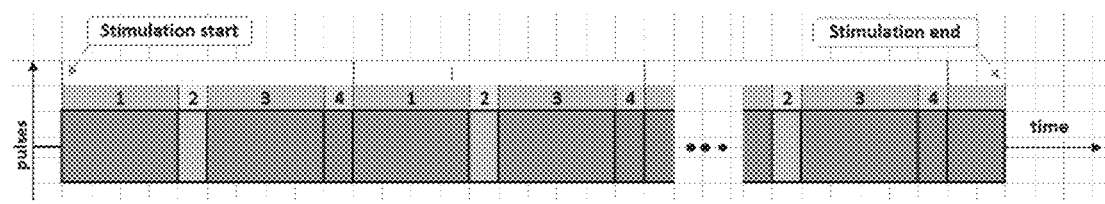
FIG. 10 illustrates exemplary shape modulation.

One or more of the waveforms may have a pulse shape that is modulated over time. In a variation illustrated in FIG. 10, the pulse shape may be cycled between four periods. The first period may comprise a two-phase current-controlled waveform with symmetrical phases. The second period may comprise a current-controlled first phase, followed by a voltage-controlled second phase. This may help to preferentially stimulate a location closer to one electrode. The first phase may have a current sourced by a first electrode and sunk by a second electrode, while the second phase may have a current sourced by the second electrode and sunk by the first electrode. The third period may comprise a two-phase current-controlled waveform with symmetrical phases (i.e., the third period may be the same as the first period). The fourth period may comprise a current-controlled first phase, followed by a voltage-controlled second phase. The first phase may have a current sourced by the second electrode and sunk by the first electrode, while the second phase may have a current sourced by the first electrode and sunk by the second electrode. In each period, the pulses may be charged-balanced. The pulse shape may be modulated at any suitable frequency, such as about 0.1 Hz.

Figure 11:
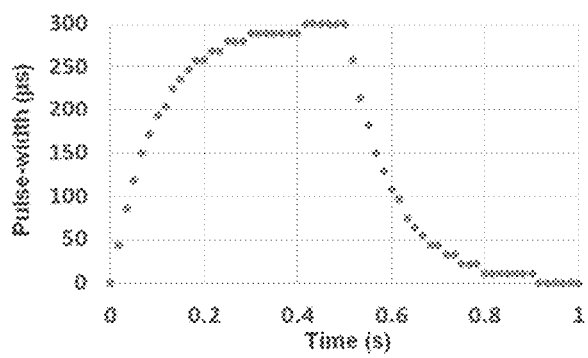
FIG. 11 illustrates exemplary pulse width modulation.

One or more of the waveforms may have a pulse width that is modulated over time. In one variation, the pulse width of the current-controlled phases may be modulated from 0 µs to 300 µs. The modulation may follow an exponential function that describes the increase and decrease of the pulse width over time, as illustrated in FIG. 11 and as described in more detail with respect to FIG. 8.

Figure 12A:
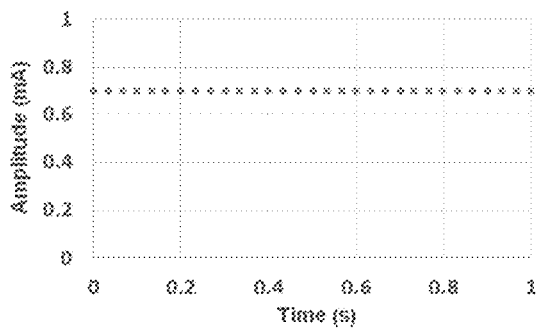
FIGS. 12A-12E illustrate exemplary modulations of amplitude and frequency waveform parameters.

One or more of the waveforms may have a maximum amplitude that is modulated over time. The amplitude modulation of the current-controlled phases may approximate a triangular shape, a rectangular shape, or any other suitable shape. Exemplary amplitude modulations at various frequencies are illustrated in FIGS. 12A-12E, which show amplitude modulations having a rectangular shape (FIG. 12B) and amplitude modulations that approximate triangular shapes (12C-12E). The maximum amplitude may be modulated at any suitable frequency, such as between about 0.5 Hz and about 3 Hz. It should be appreciated that in some other variations, the maximum amplitude may be constant, as shown in FIG. 12A.

FIGS. 13A-13E depict exemplary waveforms 1310, 1320, 1330, 1340, and 1350, respectively, wherein one or more of these parameters are modulated over time, where each type of modulation is independent from and concurrent with the other types of modulation. Boxes 1302, 1304, and 1306 on FIG. 13E highlight modulation of shape, pulse width, and maximum amplitude, respectively. In some variations (e.g., those of FIGS. 13B-13E) all three of shape, pulse width, and maximum amplitude are modulated over time, but it should be appreciated that in other variations of the waveform (e.g., that of FIG. 13A), only one or two of these parameters may be modulated over time.

The five waveforms of FIGS. 13A-13E may be available on the stimulator (e.g., stimulator 400 described above with respect to FIGS. 4A-4C, or microstimulator 200 described above with respect to FIGS. 2A-2C), and the stimulator may be configured such that the patient can use a user interface (e.g., an interface comprising two buttons) to select between the five different waveforms. In some variations of the device, when the device is used for a treatment period, turned off, and turned back on for an additional treatment period, the device may automatically turn on to the last stimulation setting used.

Figure 13A:
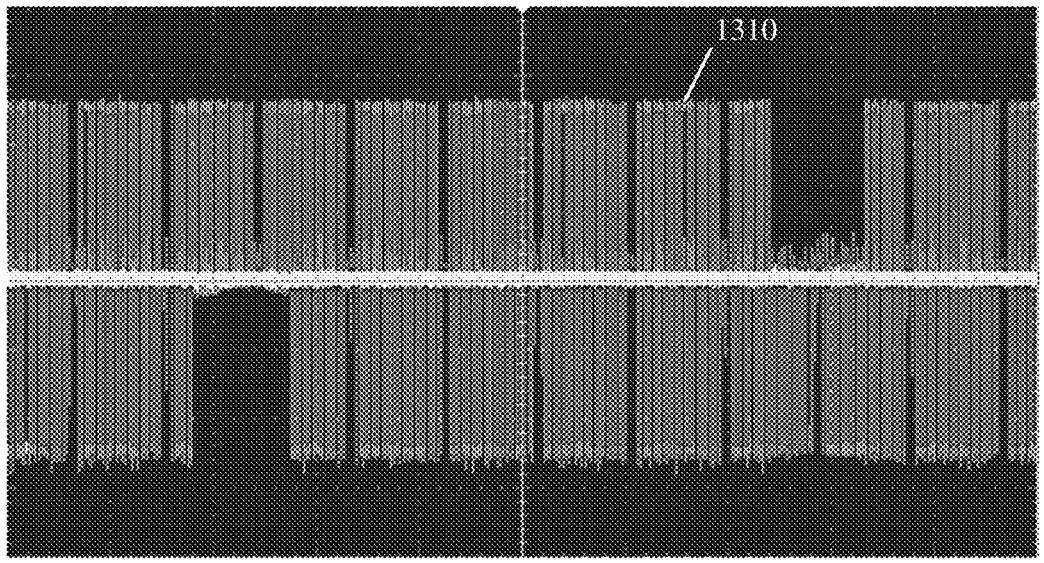
FIGS. 13A-13E depict exemplary waveforms showing multiple parameters that are concurrently modulated over time.

Setting 1, illustrated in FIG. 13A, may have a stimulation frequency of 30 Hz; a minimum stimulation current amplitude of 0.7 mA, a maximum stimulation current amplitude of 0.7 mA, and thus no variation in maximum stimulation current amplitude (as shown in FIG. 12A); a minimum pulse width of 0 µs; a maximum pulse width of 300 µs; a pulse width modulation frequency of 1 Hz (rising and falling according to an exponential function, as shown in FIG. 11); a minimum charge injection per phase (at 0 µs pulse width) of 0 µC; a maximum charge injection per phase (at 0.7 mA and 300 µs) of 0.21 µC; and a pulse shape that is modulated as described above with respect to FIG. 10.

Figure 12B:
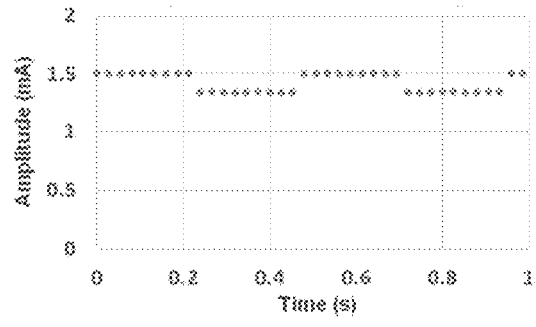
Figure 13B:
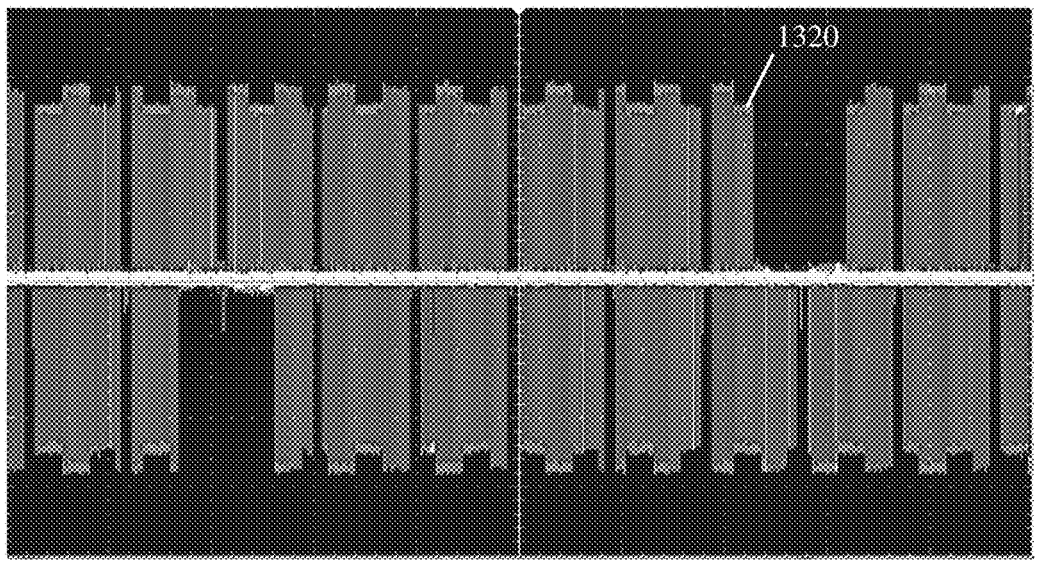

Setting 2, illustrated in FIG. 13B, may have a stimulation frequency of 37.5 Hz; a minimum stimulation current amplitude of 1.33 mA, a maximum stimulation current amplitude of 1.5 mA, a variation in maximum stimulation current amplitude of 0.17 mA, and an amplitude modulation frequency of 2.1 Hz (as shown in FIG. 12B); a minimum pulse width of 0 µs; a maximum pulse width of 300 µs; a pulse width modulation frequency of 1 Hz (rising and falling according to an exponential function, as shown in FIG. 11); a minimum charge injection per phase (at 0 µs pulse width) of 0 µC; a maximum charge injection per phase (at 1.5 mA and 300 µs) of 0.45 µC; and a pulse shape that is modulated as described above with respect to FIG. 10.

Figure 12C:
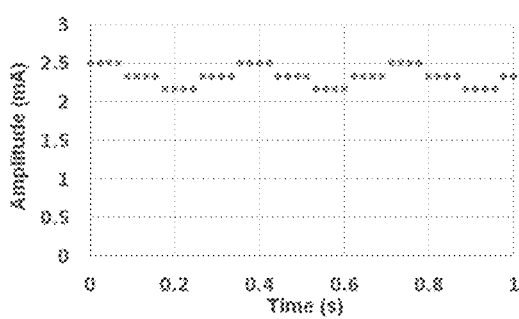
Figure 13C:
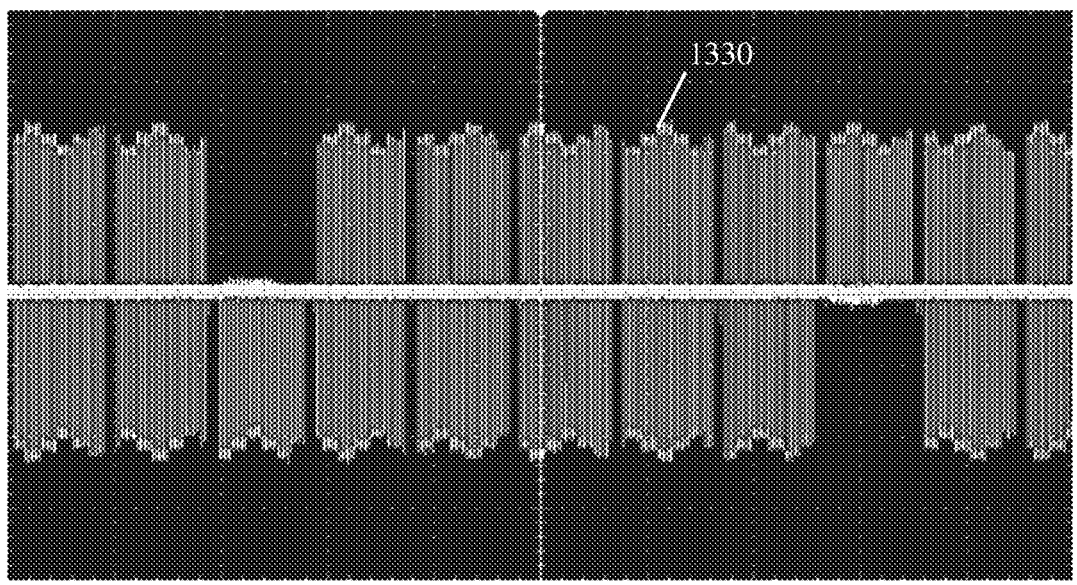

Setting 3, illustrated in FIG. 13C, may have a stimulation frequency of 45 Hz; a minimum stimulation current amplitude of 2.17 mA, a maximum stimulation current amplitude of 2.5 mA, a variation in maximum stimulation current amplitude of 0.33 mA, and an amplitude modulation frequency of 2.6 Hz (as shown in FIG. 12C); a minimum pulse width of 0 µs; a maximum pulse width of 300 µs; a pulse width modulation frequency of 1 Hz (rising and falling according to an exponential function, as shown in FIG. 11); a minimum charge injection per phase (at 0 µs pulse width) of 0 µC; a maximum charge injection per phase (at 2.5 mA and 300 µs) of 0.75 µC; and a pulse shape that is modulated as described above with respect to FIG. 10.

Figure 12D:
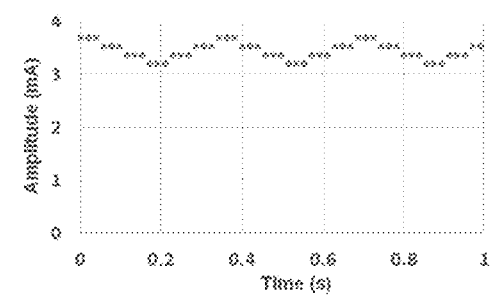
Figure 13D:
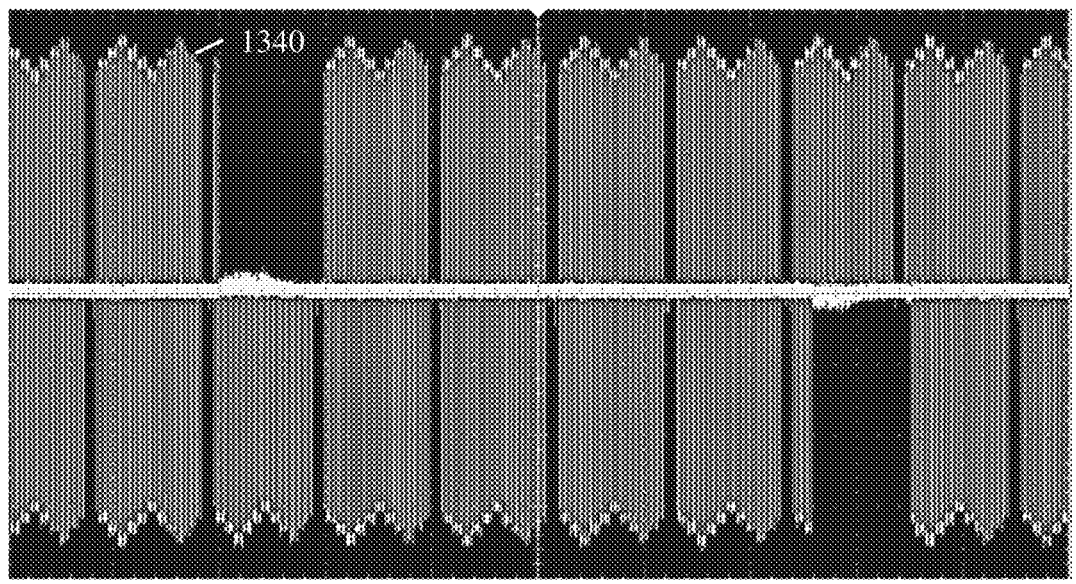

Setting 4, illustrated in FIG. 13D, may have a stimulation frequency of 52.5 Hz; a minimum stimulation current amplitude of 3.2 mA, a maximum stimulation current amplitude of 3.7 mA, a variation in maximum stimulation current amplitude of 0.5 mA, and an amplitude modulation frequency of 2.8 Hz (as shown in FIG. 12D); a minimum pulse width of 0 µs; a maximum pulse width of 300 µs; a pulse width modulation frequency of 1 Hz (rising and falling according to an exponential function, as shown in FIG. 11); a minimum charge injection per phase (at 0 µs pulse width) of 0 µC; a maximum charge injection per phase (at 3.7 mA and 300 µs) of 1.11 µC; and a pulse shape that is modulated as described above with respect to FIG. 10.

Figure 12E:
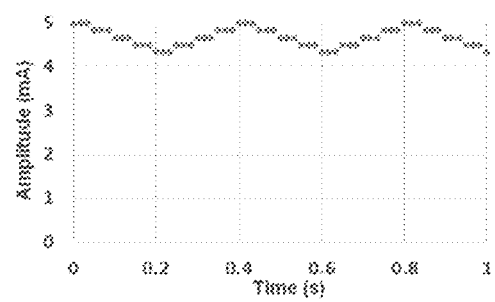
Figure 13E:
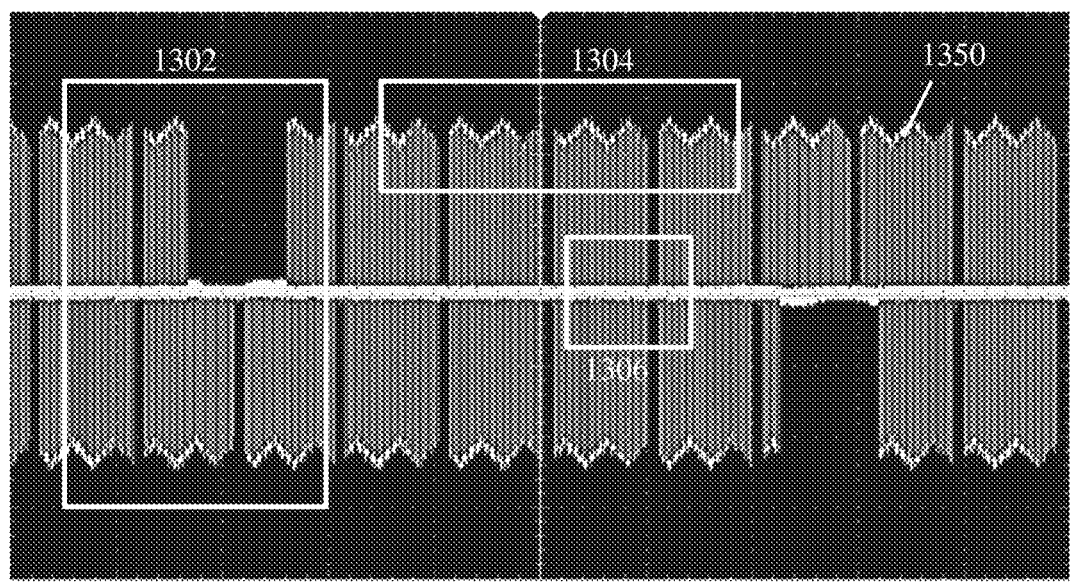

Setting 5, illustrated in FIG. 13E, may have a stimulation frequency of 60 Hz; a minimum stimulation current amplitude of 4.3 mA, a maximum stimulation current amplitude of 5.0 mA, a variation in maximum stimulation current amplitude of 0.67 mA, and an amplitude modulation frequency of 2.5 Hz (as shown in FIG. 12E); a minimum pulse width of 0 µs; a maximum pulse width of 300 µs; a pulse width modulation frequency of 1 Hz (rising and falling according to an exponential function, as shown in FIG. 11); a minimum charge injection per phase (at 0 µs pulse width) of 0 µC; a maximum charge injection per phase (at 5.0 mA and 300 µs) of 1.5 µC; and a pulse shape that is modulated as described above with respect to FIG. 10.

Through patterned waveforms having these parameter combinations, a large parameter space may be provided on a single device with a simple user interface and a limited number of settings. This may increase the ability of a single device having a limited number of preset waveforms to deliver a waveform that is as effective or nearly as effective for an individual patient as a waveform in which parameters are individually tuned for each patient.

Anatomical Targets

In some variations, it may be desirable to deliver the electrical stimuli described herein to one or more nerves that innervate the lacrimal gland tissue. In some variations, it may be desirable to deliver the electrical stimuli described herein to the nasal mucosa. This may cause lacrimation by activating the nasolacrimal reflex. In some instances, the targeted area may comprise tissue innervated by the anterior ethmoidal branch of the nasociliary nerve. In another variation, the anatomical structure is the posterior ethmoid nerve. In some instances, the targeted area of the nasal mucosa may be superior to the columella. In some of these instances, the targeted area may be near the inferior end of the nasal bone (i.e., near the interface between the nasal bone and the upper lateral cartilage). In other variations, the targeted area may be the columella. In some variations, it may be desirable to deliver the stimulus between about 20 mm and about 35 mm into the nasal cavity of the patient. In some of these variations, it may be desirable to place an electrode between about 25 mm and about 35 mm into the nasal cavity of the patient. It may be desirable that the stimulus be delivered in the anterior portion of the nasal cavity, within the nostrils and anterior to the turbinates, and in some instances, at a location anterior to the middle turbinate, or at a location anterior to the inferior turbinate. It may in some instances be desirable to direct stimulus such that a portion is directed toward the front of the nose. The stimulus may be delivered at least partially through tissue of or near the septum. This may allow for selective activation of nerves in the front of the septum (e.g., the ophthalmic branch of the trigeminal nerve) while minimizing activation of nerves toward the rear of the nasal septum, which may reduce negative side effects that may occur from stimulation of nerves that innervate the teeth, and which may reduce rhinorrhea. It may also in some instances be desirable to direct the stimulus so as to reduce negative side effects that may occur from stimulation of the olfactory area.

Other exemplary anatomical structures may include nerves, muscles, mucosal or sub-mucosal tissues (e.g., nasal or sinus mucosa or sub-mucosa), sensory cells in the glaborous and hairy skin, glands or other structures of a patient involved in the process of lacrimation or glandular vasodilation that may be electrically stimulated. For example, the anatomical structures may include, but are not limited to, a lacrimal gland, one or more meibomian glands, lacrimal ducts, cutaneous receptors (mechanoreceptors, Meissner's corpuscles, neurotendinous spindles, golgi tendon organs, Ruffini's corpuscles, Stretch Receptors, Ruffini corpuscle end-organs, Pacinian corpuscle end-organs, hair follicle receptors, free nerve endings, thermoreceptors, bulboid or Krause corpuscles, nociceptors), parasympathetic nerves, fibers and neurites, sympathetic nerves, fibers and neurites, rami lacrimales, lacrimal nerve, perivascular nerves of lacrimal artery and branches thereof, nerve fibers innervating the meibomian glands, myoepithelial cells of the lacrimal gland, acinar cells of the lacrimal gland, ductal cells of the lacrimal gland. In yet a further variation, the anatomical structure is the infra-trochlear nerve. In other variations, the anatomical structure is a cutaneous receptor responsible for sensing changes in force or temperature over time or a set of cutaneous receptors in an area of the skin reporting changes in force applied to the skin directly or indirectly by moving hair growing in the skin, or the nerves innervating the cutaneous receptors reporting changes in force applied to the skin or hair in the skin, or temperature changes in the skin including the mucosa, the sub-mucosa in the nose or the conjunctiva in the eye.

Stimuli comprising the waveforms described herein may be delivered to these anatomical targets using stimulators such as those described herein according to treatment regimens described in U.S. patent application Ser. No. 13/441,806, which was previously incorporated by reference in its entirety, and in U.S. patent application Ser. No. 14/256,915, which was previously incorporated by reference in its entirety.

EXAMPLES

The following examples further illustrate the electrical stimulation patterns and their effects as disclosed herein, and should not be construed in any way as limiting their scope.

Example 1

Stimulation Using a Lacrimal Implant

Patients having microstimulators implanted in an ocular region were tested with 30 Hz non-patterned stimulation (control) and with on/off patterns (1 second on/1 second off, 2 seconds on/2 seconds off, and 5 seconds on/5 seconds off) at different frequencies (30 Hz, 70 Hz, and 155 Hz). The implanted microstimulators had the features shown in FIGS. 2A-2C and described herein.

Patient perception of the stimulus differed between the 30 Hz non-patterned waveform control and patterned waveforms. Specifically, whereas 3 patients receiving the 30 Hz non-patterned waveform felt that their perception of the waveform faded over the stimulation period, when receiving patterned waveforms, no patients reported perception of the waveform fading over the stimulation period. When the stimulus was a 30 Hz, 1 second on/off waveform ("Pattern 1"), 3 patients perceived the waveform as continuous, while 15 perceived the waveform as intermittent. When the stimulus was a 30 Hz, 5 second on/off waveform ("Pattern 2"), all patients perceived the waveform as intermittent. When the stimulus was a 70 Hz, 1 second on/off waveform ("Pattern 3"), 2 patients perceived the waveform as continuous, and 10 perceived the waveform as intermittent. Patients reported that they perceived Pattern 3 as "stronger," "faster," and "sharper" than the other waveforms. When the stimulus was a 155 Hz, 1 second on/off waveform ("Pattern 4"), whether patients perceived the waveform as continuous or intermittent was amplitude-dependent, and qualitative perceptions ranged, including reports of the waveform as "weaker," "strong," or a "pinch."

Figure 14A:
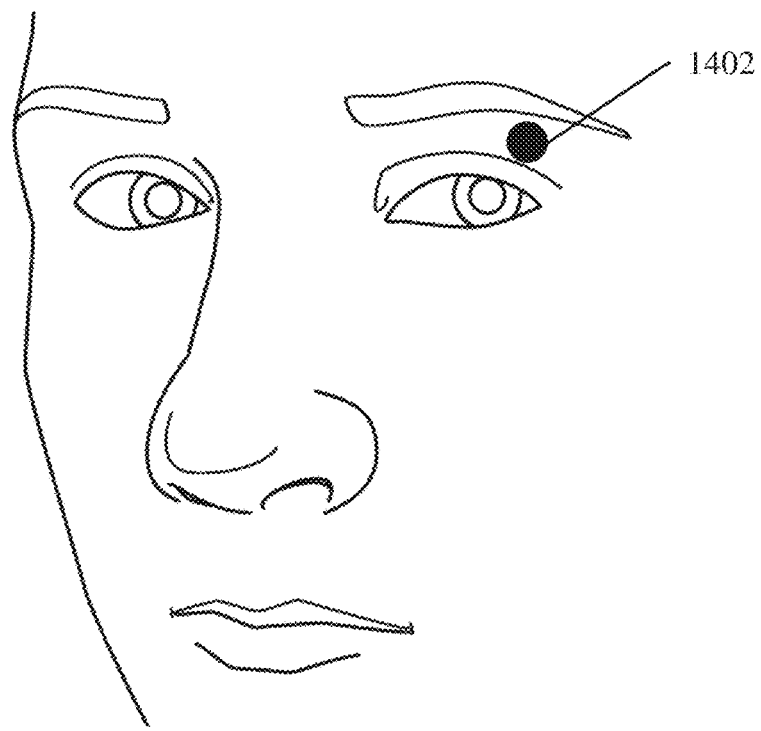
FIG. 14A depicts paresthesia felt with stimulation applied at 30 Hz (non-patterned).
Figure 14B:
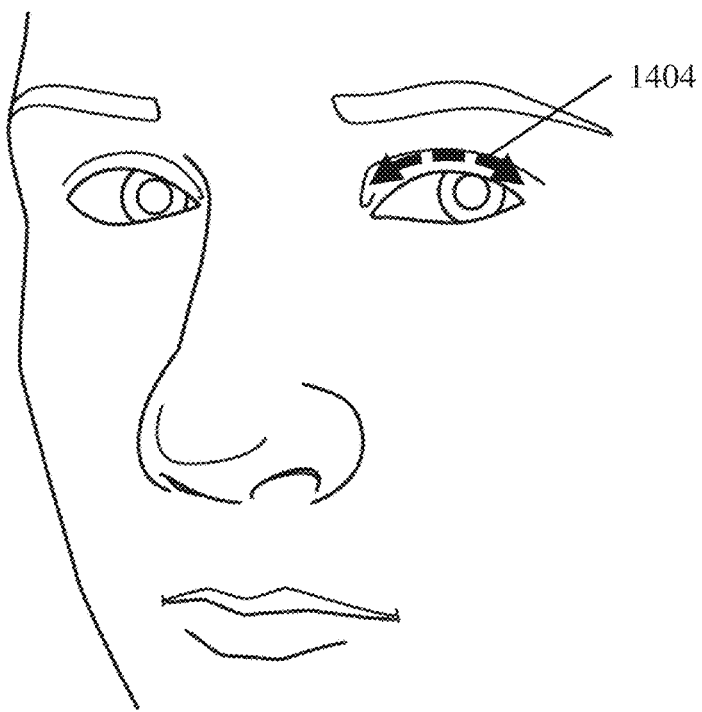
FIG. 14B illustrates an exemplary moving paresthesia obtained with waveform patterning.
Figure 14C:
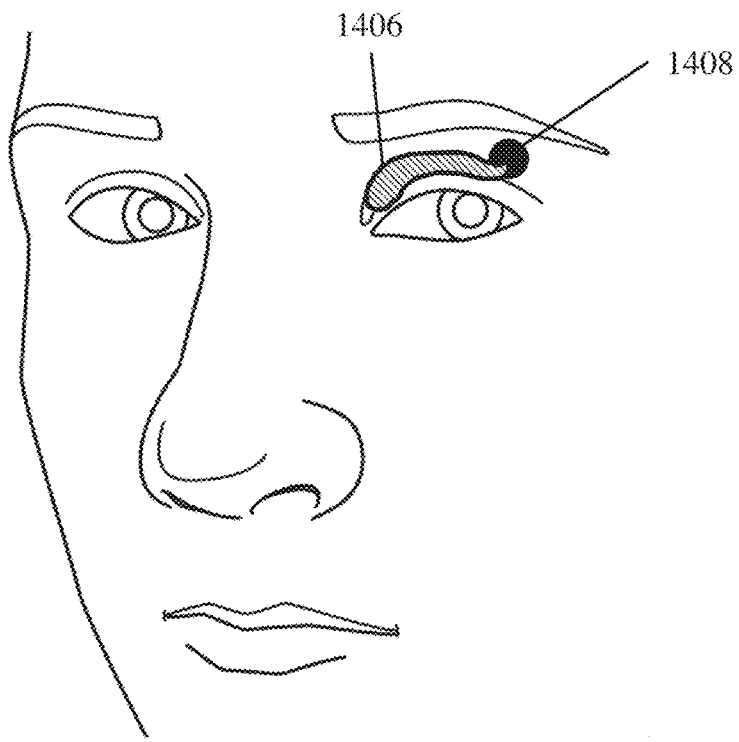
FIG. 14C illustrates another exemplary moving paresthesia obtained with waveform patterning.
Figure 14D:
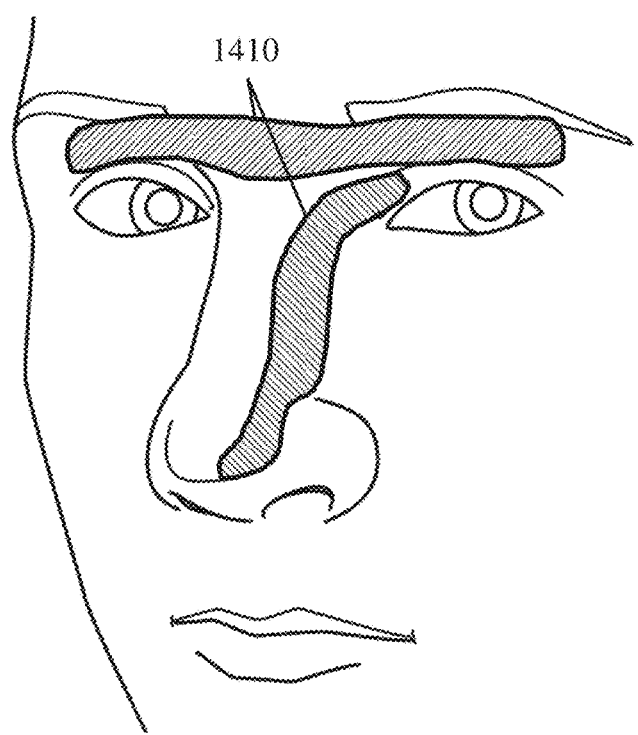
FIG. 14D depicts paresthesia felt by waveform patterning.

Moreover, patients reported a change in the quality and/or location of paresthesia. FIG. 14A depicts the area 1402 of paresthesia felt with stimulation using the 30 Hz non-patterned waveform. With the patterned waveforms, patients felt movement of the paresthesia (in the form of vibration and/or tickle), as shown in FIG. 14B (the vibration and/or the tingle moved along their eyelid in the directions of the arrows 1404). Some patients felt continuously present vibration in one area 1408 and continuously present or partially appearing and reappearing sensation or tickle in other areas 1406, as shown in FIG. 14C. Other patients experienced an increase in affected area with paresthesia with patterned waveforms, shown in FIG. 14D as area 1410 extending along one or both of the eyebrows and/or along or in the nose.

Patient perceptions after cessation of stimulation also differed between the 30 Hz non-patterned waveform and the patterned waveforms. Whereas patients did not perceive paresthesia after cessation of the control, patients reported perceiving paresthesia in the form of a tingling sensation after cessation of Patterns 1, 3, and 4.

Schirmer scores increased with patterned waveforms as compared to the 30 Hz non-patterned waveform control. With Pattern 1, one third of patients had Schirmer scores that increased by 50%. With Pattern 3, three quarters of patients had Schirmer scores that increased by 50-100%. With Pattern 4, three eighths of patients had Schirmer scores that increased by 100% or more.

Some of the patterned waveforms also provided additional advantages. For example, Pattern 1 used less power than the control while also reducing patient accommodation; and Pattern 4 allowed for both nerve stimulation and block.

Example 2

Stimulation Using a Lacrimal Implant (2)

Figure 15:
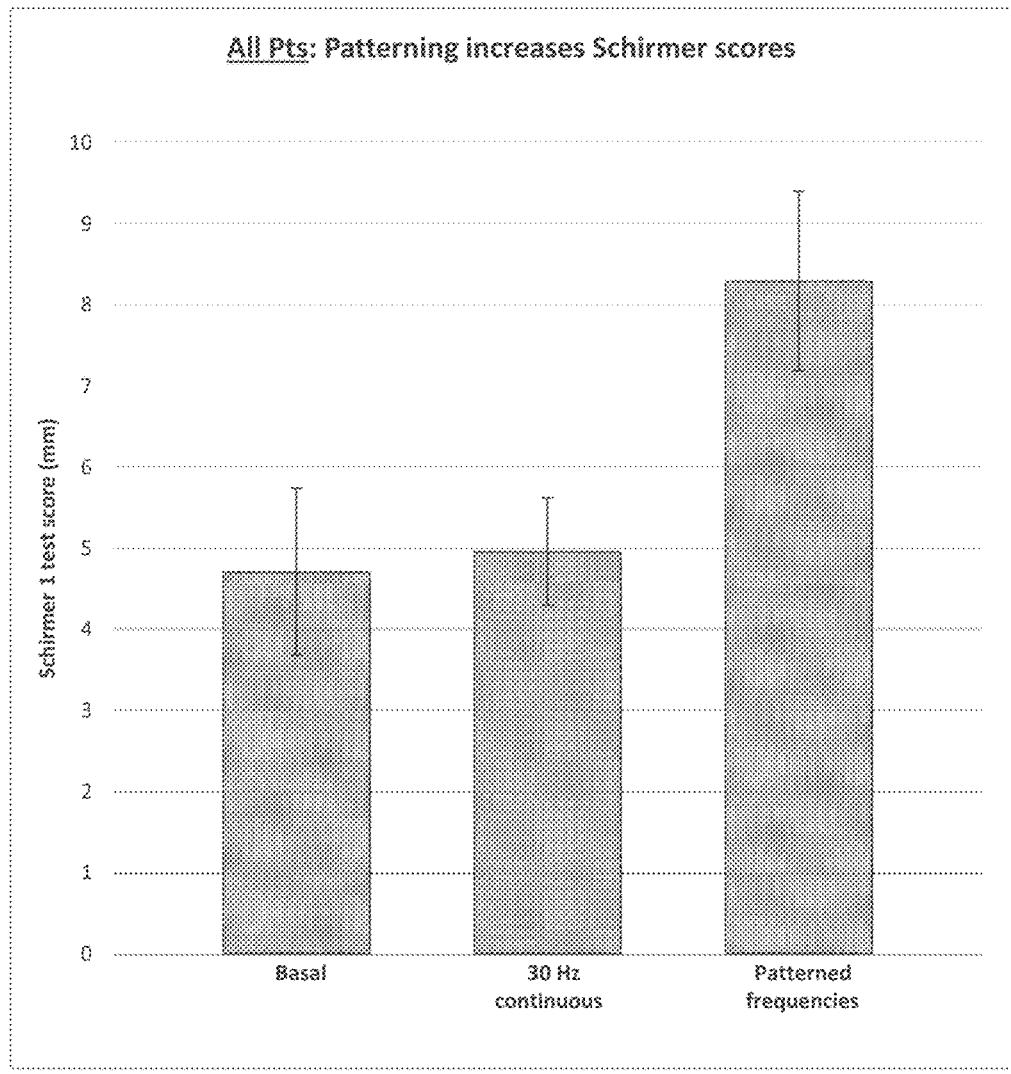
FIG. 15 is a bar-chart diagram comparing tearing results from basal tearing (left, no stimulation) to 30 Hz non-patterned waveform stimulation (middle) to patterned, patient-optimized stimulation waveforms (right).

In patients having a microstimulator implanted in an ocular region, use of patterned waveforms generated an increase in lacrimation as measured by Schirmer's test in comparison to basal tearing (control 1=no electric stimulation) and in comparison to stimulation at 30 Hz (non-patterned) (control 2). The implanted microstimulators had the features shown in FIGS. 2A-2C and described herein. The data is provided below in Table 2, and a bar-chart diagram comparing averaged tearing results from basal tearing (left, no stimulation) to 30 Hz non-patterned waveform stimulation (middle) to patterned, patient-optimized stimulation waveforms (right) is shown in FIG. 15. Based on the data in Table 2, the averaged value for basal tearing was 4.71 mm, the averaged value was 4.96 mm for non-patterned stimulation at 30 Hz, and the average value was 8.29 mm when patterned stimulation was used. Overall, the increase in average Schirmer score using non-patterned stimulation at 30 Hz was about 5% as compared to basal tearing, and the increase in average Schirmer score using patterned waveforms was about 76% as compared to basal tearing. Thus, patient-optimized pattered waveforms were able to increase tearing by a much greater amount (in this case, over 70 percentage points) than a 30 Hz non-patterned waveform.

TABLE 2

Schirmer Scores from 12 Patients.

| Implanted Side | Basal Schirmer Score (mm) | | | 30 Hz Non-Patterned Schirmer Score (mm) | | | Patterned Schirmer Score (mm) | | | Patterned Waveform |
|---|---|---|---|---|---|---|---|---|---|---|
| | L | R | Ave | L | R | Ave | L | R | Ave | |
| R | 8 | 5 | 6.5 | 3 | 4 | 3.5 | 8 | 5 | 6.5 | 30 Hz amplitude modulated by about 30% |
| L | 3 | 8 | 5.5 | 3 | 5 | 4 | 5 | 8 | 6.5 | 70 Hz amplitude modulated by about 30% |
| L | 3 | 2 | 2.5 | 3 | 5 | 4 | 3 | 8 | 5.5 | 70 Hz 1 sec on, 1 sec off |
| L | 2 | 3 | 2.5 | 5 | 5 | 5 | 5 | 3 | 4 | 70 Hz amplitude modulated by about 30% |
| L | 12 | 18 | 15 | 10 | 9 | 9.5 | 13 | 19 | 16 | 30 Hz amplitude modulated by 100% |
| L | 4 | 3 | 3.5 | 6 | 6 | 6 | 7 | 7 | 7 | 70 Hz amplitude modulated by about 30% |
| R | 2 | 3 | 2.5 | 3 | 3 | 3 | 8 | 7 | 7.5 | 30 Hz 1 sec on, 1 sec off |
| L | 5 | 7 | 6 | 5 | 5 | 5 | 8 | 8 | 8 | 70 Hz 1 sec on, 1 sec off |
| L | 2 | 2 | 2 | 2 | 1 | 1.5 | 5 | 5 | 5 | 70 Hz amplitude modulated by about 30% |
| R | 4 | 2 | 3 | 12 | 6 | 9 | 18 | 12 | 15 | 30 Hz 5 sec on, 5 sec off |
| L | 4 | 2 | 3 | 7 | 2 | 4.5 | 7 | 7 | 7 | 30 Hz 1 sec on, 1 sec off |
| L | 4 | 5 | 4.5 | 5 | 4 | 4.5 | 7 | 16 | 11.5 | frequency-modulated 30 Hz to 70 Hz randomized |

The patterned waveforms were also capable of generating paresthesia in patients in whom paresthesia was not felt during stimulation or who only experienced short-lived paresthesia (e.g., less than 30 seconds, often only less than 10 seconds, of paresthesia felt even though stimulation was supplied continuously). The newly acquired or re-acquired paresthesia was further accompanied by increases in lacrimation and improved patient satisfaction.

Patients often reported the feeling of vibration during stimulation and tingle during stimulation pauses (for example, during off portions of waveforms having a 1 second on/1 second off pattern), and in certain cases for seconds or minutes after the stimulation had stopped after application. There were several reports of patients feeling that the vibration or the tingle moved physically along their eyelid and eyebrow, in two cases even in their nasal area (outside and/or inside the nose). Patient reception was generally very positive.

Example 3

Stimulation Using a Lacrimal Implant (3)

Nineteen patients had microstimulators implanted in an ocular region. (Twelve of these patients are the same patients as in Example 2.) For each patient, a patient-optimized patterned waveform was determined by modulating waveform frequency, pulse width, and on/off periods while gathering patient feedback in order to maximize the reported paresthesia in the area of the orbit, as described above.

Each waveform was provided using the same controller/energizer for each patient. The waveforms tested for each patient included:
30 Hz
30 Hz, 1 second on, 1 second off
30 Hz, 5 seconds on, 5 seconds off
70 Hz, 1 second on, 1 second off
30 Hz, pulse-width modulated from 100% to 0% and back to 100% in 1 sec
30 Hz, pulse-width modulated from 100% to 70% and back to 100% in 1 sec
70 Hz, pulse-width modulated from 100% to 70% and back to 100% in 1 sec
frequency modulated from 30 Hz to 70 Hz in an approximately linear fashion by steps of 5 Hz (i.e., for the increasing portion of the frequency modulation, 30 Hz, 35 Hz, 40 Hz, 50 Hz, 55 Hz, 60 Hz, 65 Hz, 70 Hz), modulated up and down in 1 sec (from 70 to 30 and back to 70 in one second)
frequency modulated from 30 Hz to 70 Hz in a random fashion, with frequencies 5 Hz apart (30 Hz, 35 Hz, 40 Hz, 45 Hz, 55 Hz, 60 Hz, 65 Hz, 70 Hz)

Patients were asked a series of questions for each waveform, including:
whether the waveform was causing discomfort;
how they would compare the sensation from the waveform to other waveforms, including 30 Hz non-patterned waveform, and any other waveforms previously tested on the same day;
whether they had the sensation of their eyes getting wet;
whether they felt a combination of a tickle and vibration;
whether the sensation (tickle and/or vibration) felt as though it was moving (this suggests less likelihood of accommodation); and
the location of the sensation.

It was desirable that the patient feel sensation in the upper eyelid, since this was considered likely to correspond with activating the lacrimal and the frontal nerves in the orbit. The closer the sensation was to the eye itself and the larger the area of paresthesia, the more optimal a waveform was rated. Additionally, waveforms that were perceived as a mixture of tickle and vibration sensations in locations that corresponded with the sensory pathways of the ophthalmic branch of the trigeminal nerve (CN V1) were desirable. These locations included not only the eyelid, but also the eyebrow, the temple area of the forehead, the nose (especially the inside of the nose), and certain areas of the forehead.

For each patient, three Schirmer scores were recorded: a basal Schirmer score without any stimulation ("basal Schirmer"), an acute Schirmer score during application of a 30 Hz non-patterned waveform ("30 Hz Schirmer"), and an acute Schirmer score during application of the patient-optimized patterned waveform for each patient ("patterned Schirmer").

Figure 16A:
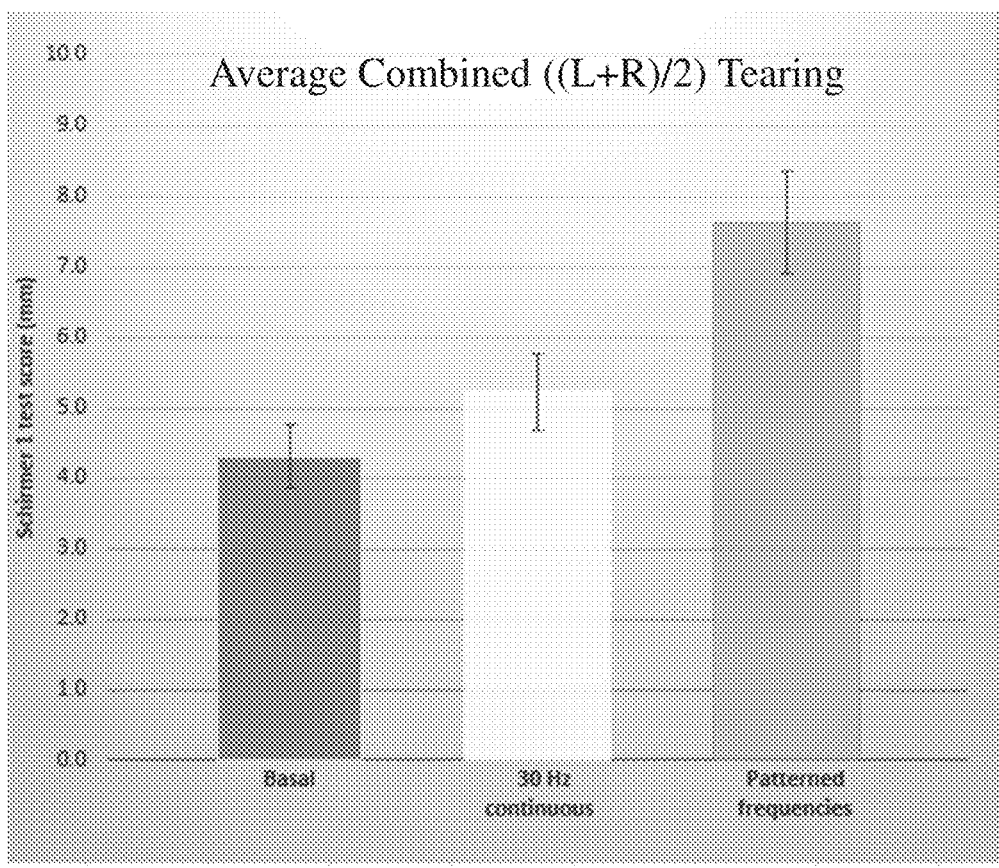
FIG. 16A shows bilateral Schirmer scores with no stimulation, 30 Hz non-patterned stimulation, and patient-specific patterned waveforms.

Average bilateral 30 Hz Schirmer scores and average bilateral patterned Schirmer scores were both higher than average bilateral basal Schirmer scores. Average bilateral patterned Schirmer scores were higher than average bilateral 30 Hz Schirmer scores. Specific data for average bilateral Schirmer scores are shown in FIG. 16A. As shown there, the 15 patients with severe DED (defined as having basal Schirmer scores <10 mm) averaged a 22% increase over basal Schirmer scores for 30 Hz Schirmer scores and a 78% increase over basal Schirmer scores for patterned Schirmer scores.

Figure 17A:
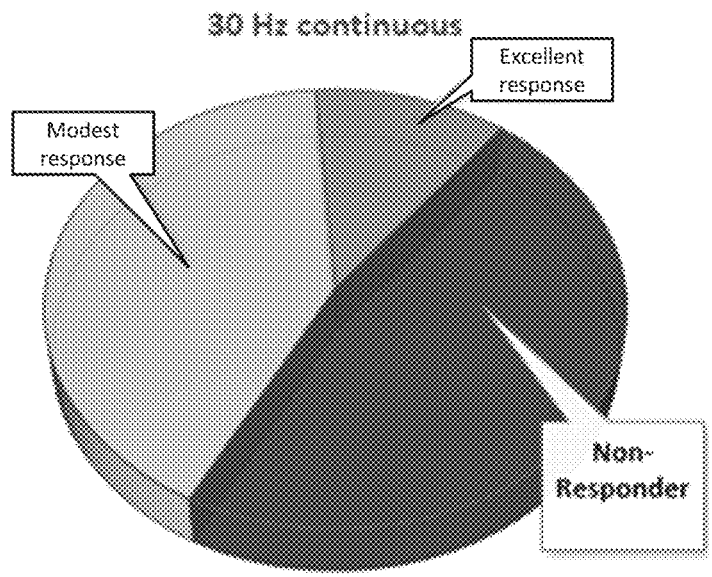
FIGS. 17A-17B show bilateral responses to 30 Hz non-patterned stimulation (17A) and patient-specific patterned waveforms (17B).
Figure 17B:
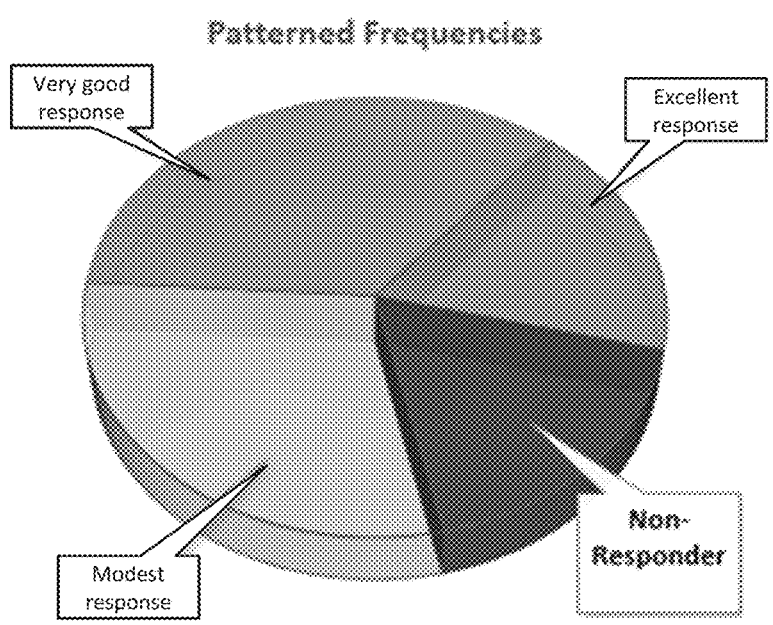

More patients showed increased bilateral Schirmer scores when stimulated using the patient-optimized patterned waveform than the 30 Hz non-patterned waveform. As shown in FIGS. 17A-17B, amongst the 15 patients with severe DED, the number of non-responders decreased from 47% (as shown in FIG. 17A) using the 30 Hz waveform to 20% (as shown in FIG. 17B) using the patient-optimized patterned waveform.

The comparison of ipsilateral (i.e., the eye on the same side as ocular implant), contralateral (i.e., the eye opposite the ocular implant), and bilateral (i.e., the average of both eyes) Schirmer scores indicated that stimulation from a single ocular implant resulted in bilateral tear production, but the effect was more pronounced for patient-optimized patterned waveform stimulation. Ipsilateral 30 Hz Schirmer scores were found to be higher than bilateral 30 Hz Schirmer scores, indicating that 30 Hz stimulation resulted in more tear production in the ipsilateral eye than the contralateral eye; and conversely, contralateral 30 Hz Schirmer scores were found to be lower than bilateral 30 Hz Schirmer scores, indicating that 30 Hz stimulation resulted in less tear production in the contralateral eye than the ipsilateral eye.

Figure 16B:
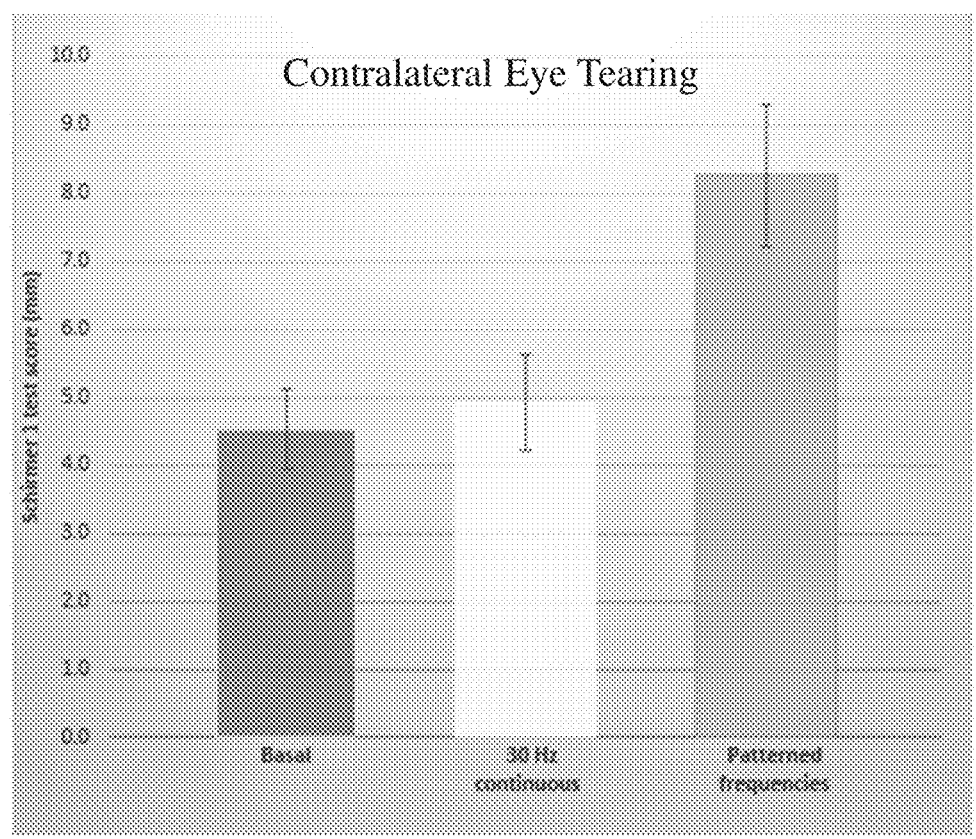
FIG. 16B shows contralateral Schirmer scores with no stimulation, 30 Hz non-patterned stimulation, and patient-specific patterned waveforms.

In contrast, both ipsilateral and contralateral patterned Schirmer scores were found to be similar to bilateral patterned Schirmer scores. This suggested that patterned stimulation better stimulated tear production in the contralateral eye than the 30 Hz stimulation, such that the patient-optimized patterned waveform was equally effective in stimulating tear production in both the ipsilateral and contralateral eyes. It was hypothesized that this was a result of the reflexive drive (activated by stimulating the lacrimal and frontal nerves) adding to the direct drive (lacrimal nerve only). FIG. 16B shows contralateral Schirmer scores for the 15 patients with severe DED. As shown there, the patients averaged a 9% increase over basal Schirmer scores for 30 Hz Schirmer scores and an 82% increase over basal Schirmer scores for patterned Schirmer scores.

By switching frequencies, either linearly or randomly, patients experienced a mixture of vibration and tickle. By changing to the higher frequency of 70 Hz at 1 second on/1 second off, modulating the frequency (30 to 70 Hz in 5 Hz increments), and/or changing the pulse width, specific patients reported the sense of tickle in addition to vibration, tickle alone or the impression of a moving vibration, often in the combination with a moving sensation of tickle. It was also found that stimulation with a patient-optimized patterned waveform allowed patients to find the location for holding the energizers/controllers in order to couple to the implant more quickly and repeatedly.

Example 4

Electrical Stimulation of the Nasal Mucosa

A patterned waveform was delivered to the nasal mucosa of subjects using a device as described with respect to FIGS. 4A-4C. The patterned waveforms delivered included the waveforms shown in FIGS. 13A-13E and described herein, as well as waveforms at 30 Hz, 70 Hz, and 155 Hz with on/off periods of 1 second on/off and 5 seconds on/off. Tear output at the same level as non-patterned stimulation was able to be achieved while reducing subject tendency to sneeze. Subjects also reported the feeling of a nasal massage that was in most cases seen as improved sensory impression. Subjects furthermore were able to use increased stimulation amplitudes during nasal stimulation leading to increased tearing without discomfort, as the maximal amplitude of charge used to stimulate was only applied for a short time. Subject reception was generally very positive.

Example 5

Frontal Nerve Stimulation (Rabbit)

Figure 18:
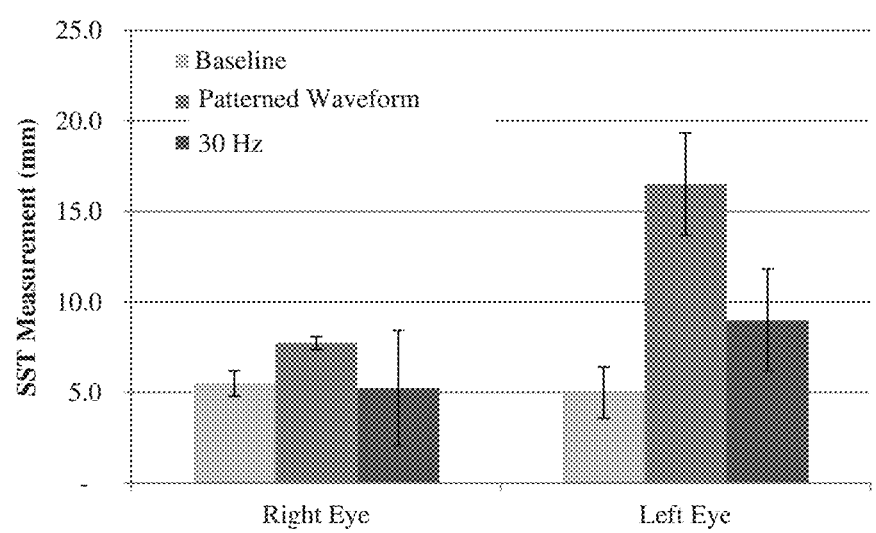
FIG. 18 shows Schirmer scores for stimulation of left frontal nerve areas in rabbits.

A rabbit was implanted with fine wire electrodes into its left frontal nerve area, and stimulation was applied at 30 Hz with amplitudes between 0.1 mA and 5.0 mA. Stimulation and baseline measurements were repeated 3 times each. As shown in Table 3 below and FIG. 18, while increased lacrimation was observed with the 30 Hz (non-patterned) waveform, the increase in lacrimation was more pronounced using a patterned stimulation with on and off periods of 10 seconds each, as measured by Schirmer scores taken during stimulus delivery.

TABLE 3

|  |  | Baseline | | Patterned Waveform | | 30 Hz | |
| --- | --- | --- | --- | --- | --- | --- | --- |
|  |  | AVG | ST DEV | AVG | ST DEV | AVG | ST DEV |
| No Stim | Right Eye | 5.5 | 0.7 | 7.8 | 0.4 | 5.3 | 3.2 |
| Stim Eye | Left Eye | 5.0 | 1.4 | 16.5 | 2.8 | 9.0 | 2.8 |

The invention claimed is:

1. A handheld system comprising one or more stimulation electrodes and a control subsystem, wherein the control subsystem comprises a programmable memory configured to store a plurality of patterned stimulation waveforms configured to generate a sensed paresthesia, and wherein at least one of the plurality of patterned stimulation waveforms comprises a pulse shape, maximum amplitude, and pulse width that are concurrently modulated over time, and wherein the pulse width is modulated over time according to an exponential function, wherein the exponential function comprises a first phase wherein the pulse width is equal to $(PW_{max}-PW_{min})(1-e^{-(t/\tau)})$, where $PW_{max}$ is the maximum pulse width, $PW_{min}$ is the minimum pulse width, and $\tau$ is a time constant.

2. The system of claim 1, wherein the exponential function comprises a second phase wherein the pulse width is equal to $(PW_{max}-PW_{min})(e^{-(t/\tau)})$.

3. The system of claim 2, wherein $PW_{max}$ is 300 µs, $PW_{min}$ is 0 µs, and $\tau$ is 0.2 µs.

* * * * *